(12) United States Patent
Fukuyama et al.

(10) Patent No.: US 11,137,398 B2
(45) Date of Patent: Oct. 5, 2021

(54) METHOD FOR ANALYZING MICROORGANISMS

(71) Applicant: Shimadzu Corporation, Kyoto (JP)

(72) Inventors: Yuko Fukuyama, Kyoto (JP); Hiroto Tamura, Kani (JP); Teruyo Kato, Aisai (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 16/274,058

(22) Filed: Feb. 12, 2019

(65) Prior Publication Data

US 2019/0250169 A1    Aug. 15, 2019

(30) Foreign Application Priority Data

Feb. 13, 2018 (JP) .............................. JP2018-023482

(51) Int. Cl.
*G01N 33/569* (2006.01)
*H01J 49/00* (2006.01)
(Continued)

(52) U.S. Cl.
CPC ............. *G01N 33/569* (2013.01); *C12Q 1/04* (2013.01); *G01N 33/6851* (2013.01);
(Continued)

(58) Field of Classification Search
CPC ............. G01N 33/569; G01N 33/6851; G01N 33/6848; C12Q 1/04; H01J 49/0027
See application file for complete search history.

(56) References Cited

U.S. PATENT DOCUMENTS

2009/0137052 A1    5/2009 Kuyama et al.
2015/0136972 A1*   5/2015 Lasch ................. H01J 49/0027
                                                             250/282
(Continued)

FOREIGN PATENT DOCUMENTS

EP        1 835 282 A1    9/2007
JP     2006-189391 A      7/2006
(Continued)

OTHER PUBLICATIONS

Kuyama et al., "Sensitive detection of phosphopeptides by matrix-assisted laser desorption/ionization mass spectrometry: use of alkylphosphonic acids as matrix additives," Rapid Commun. Mass Spectrom., 2008, vol. 22, pp. 1109-1116.
(Continued)

*Primary Examiner* — Eliza W Osenbaugh-Stewart
(74) *Attorney, Agent, or Firm* — Foley & Lardner LLP

(57) ABSTRACT

In a method for analyzing a microorganism using a matrix assisted laser desorption/ionization mass spectrometer, a matrix-and-additive mixture solution prepared by mixing one or both of an alkylphosphonic acid and a surfactant with a matrix substance is used for matrix assisted laser desorption/ionization. Either an alkylphosphonic acid or a surfactant, or both of them are used as matrix additives and are mixed with the matrix substance beforehand to prepare a matrix-and-additive mixture solution. After a solution which contains a microorganism to be analyzed has been dropped onto a sample plate, the matrix-and-additive mixture solution is dropped onto that solution and dried to form a mixed crystal which contains both the constituents of the microorganism and the matrix substance. This crystal is used as a sample for MALDI-MS analysis. The sensitivity of analysis is thereby improved, without increasing the amount of time and labor required for sample preparation.

11 Claims, 24 Drawing Sheets

(51) Int. Cl.
    C12Q 1/04      (2006.01)
    G01N 33/68     (2006.01)
    G16B 50/00     (2019.01)
    H01J 49/16     (2006.01)
    G16B 40/10     (2019.01)
(52) U.S. Cl.
    CPC .......... *G16B 50/00* (2019.02); *H01J 49/0027* (2013.01); *H01J 49/164* (2013.01); *G01N 2560/00* (2013.01); *G16B 40/10* (2019.02)

(56) References Cited

U.S. PATENT DOCUMENTS

| 2016/0334420 A1 | 11/2016 | Kaneko |
| 2017/0016910 A1 | 1/2017 | Kaneko |

FOREIGN PATENT DOCUMENTS

| JP | 2009-121857 A | 6/2009 |
| JP | 2015-184020 A | 10/2015 |
| WO | WO-2015/111430 A1 | 7/2015 |

OTHER PUBLICATIONS

Meetani et al., "MALDI Mass Spectrometry Analysis of High Molecular Weight Proteins from Whole Bacterial Cells: Pretreatment of Samples with Surfactants," Journal of American Soc. Mass. Spectrom., 2005, vol. 16, pp. 1422-1426.

Nilsson, "Fingerprinting of Helicobacter pylori Strains by Matric-assisted Laser Desorption/Ionization Mass Spectrometric Analysis," Rapid Commun. Mass Spectrom., 1999, vol. 13, pp. 1067-1071.

Ohta et al., "Salt Tolerance Enhancement of Liquid Chromatography-Matrix-Assisted Laser Desorption/Ionization-Mass Spectrometry Using Matrix Additive Methylenediphosphonic Acid," Mass Spectrum (Tokyo) 2014, vol. 3: A0031, pp. 1-9.

European Search Report issued in corresponding European Patent Application No. 19156963 dated Jun. 21, 2019.

Anonymous: "Sinapinic acid", Wikipedia, Oct. 25, 2017 (Oct. 25, 2017), XP055595153, Retrieved from the Internet: URL:https://en.wikipedia.org/w/index.php? title=Sinapinic_acid&oldid=807005222 [retrieved on Jun. 7, 2019].

Notice of Reasons for Refusal dated Aug. 3, 2021 issued in corresponding JP Application No. 2018-023482, with English translation, 8 pages.

* cited by examiner

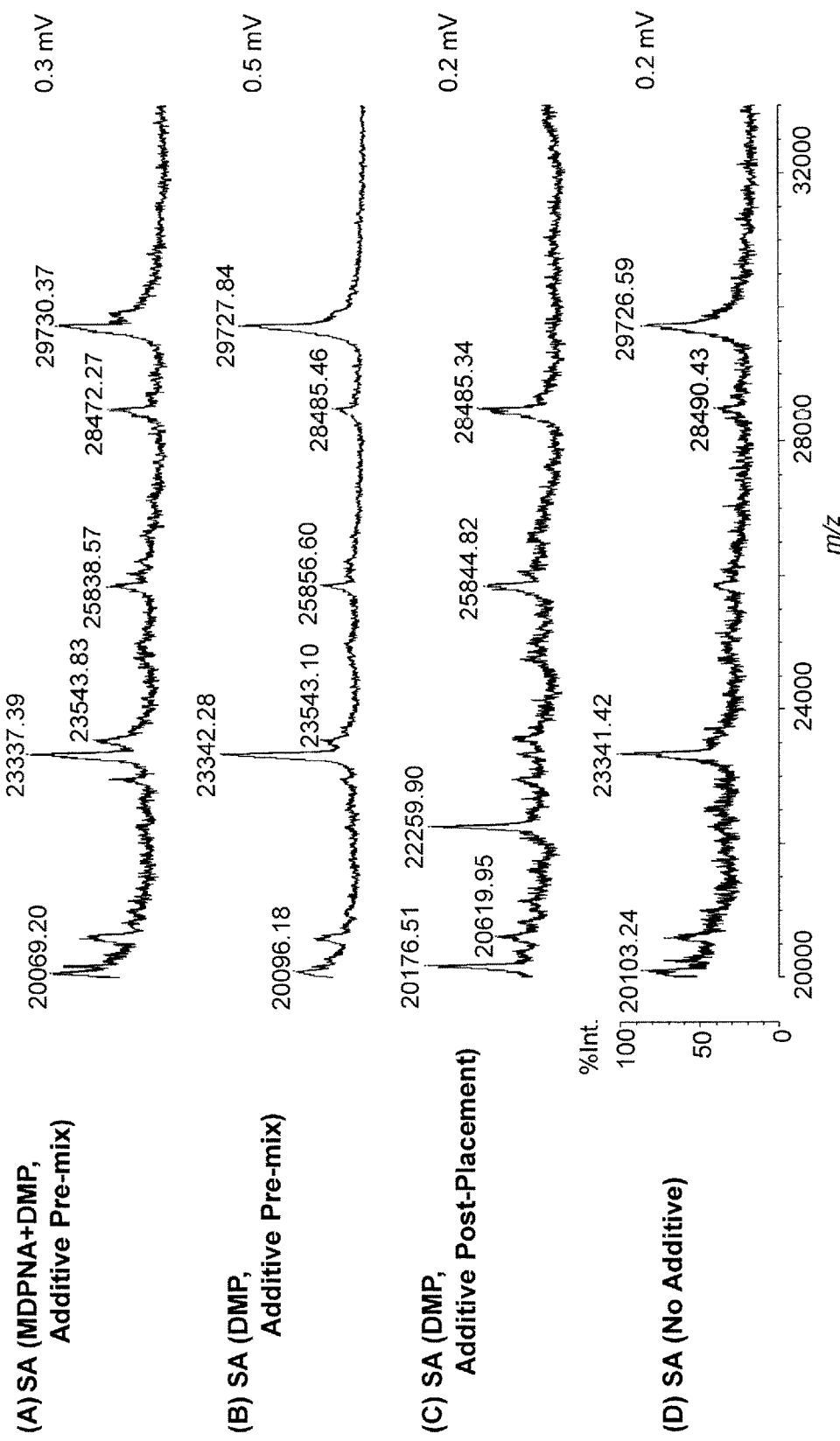

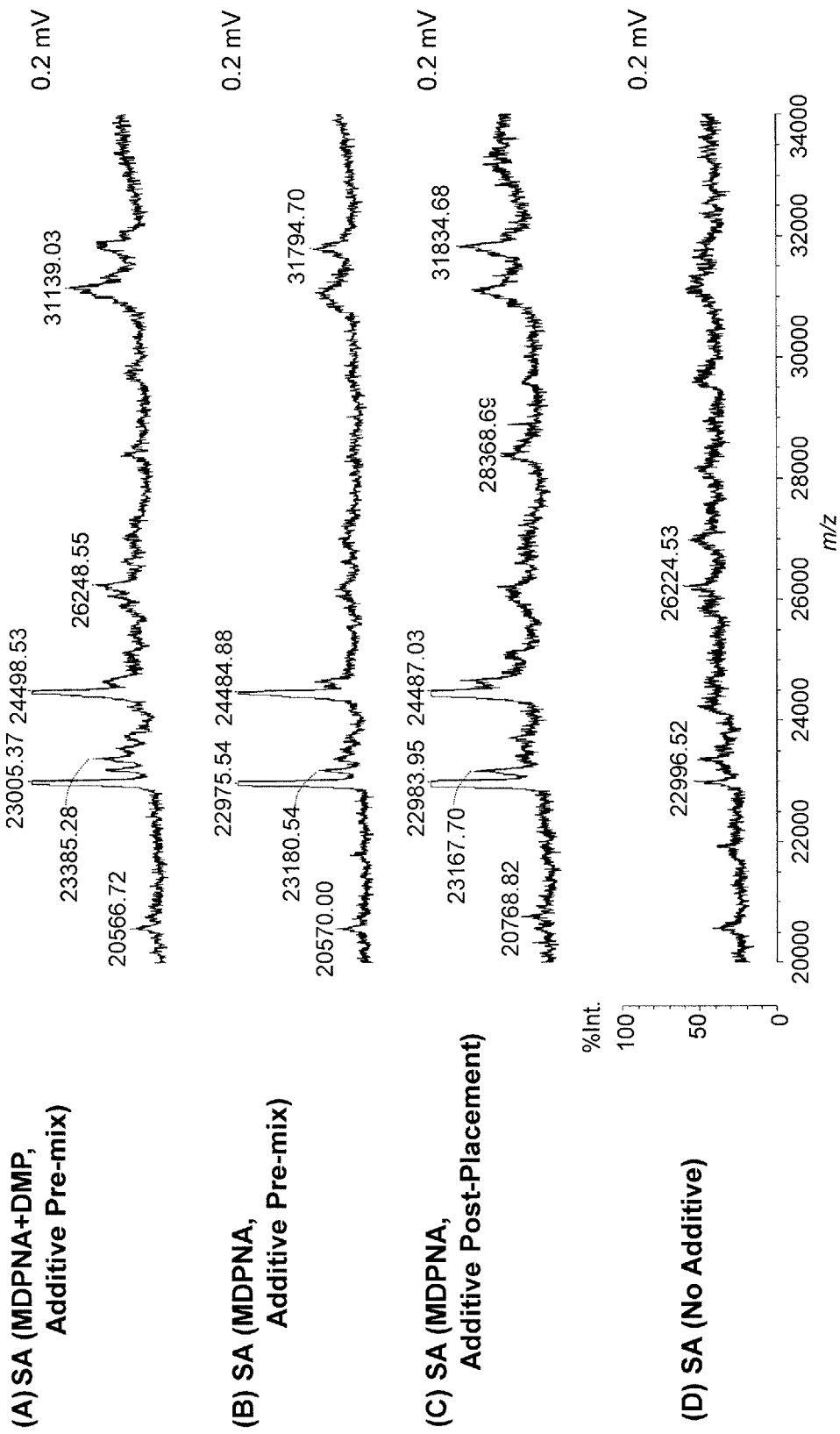

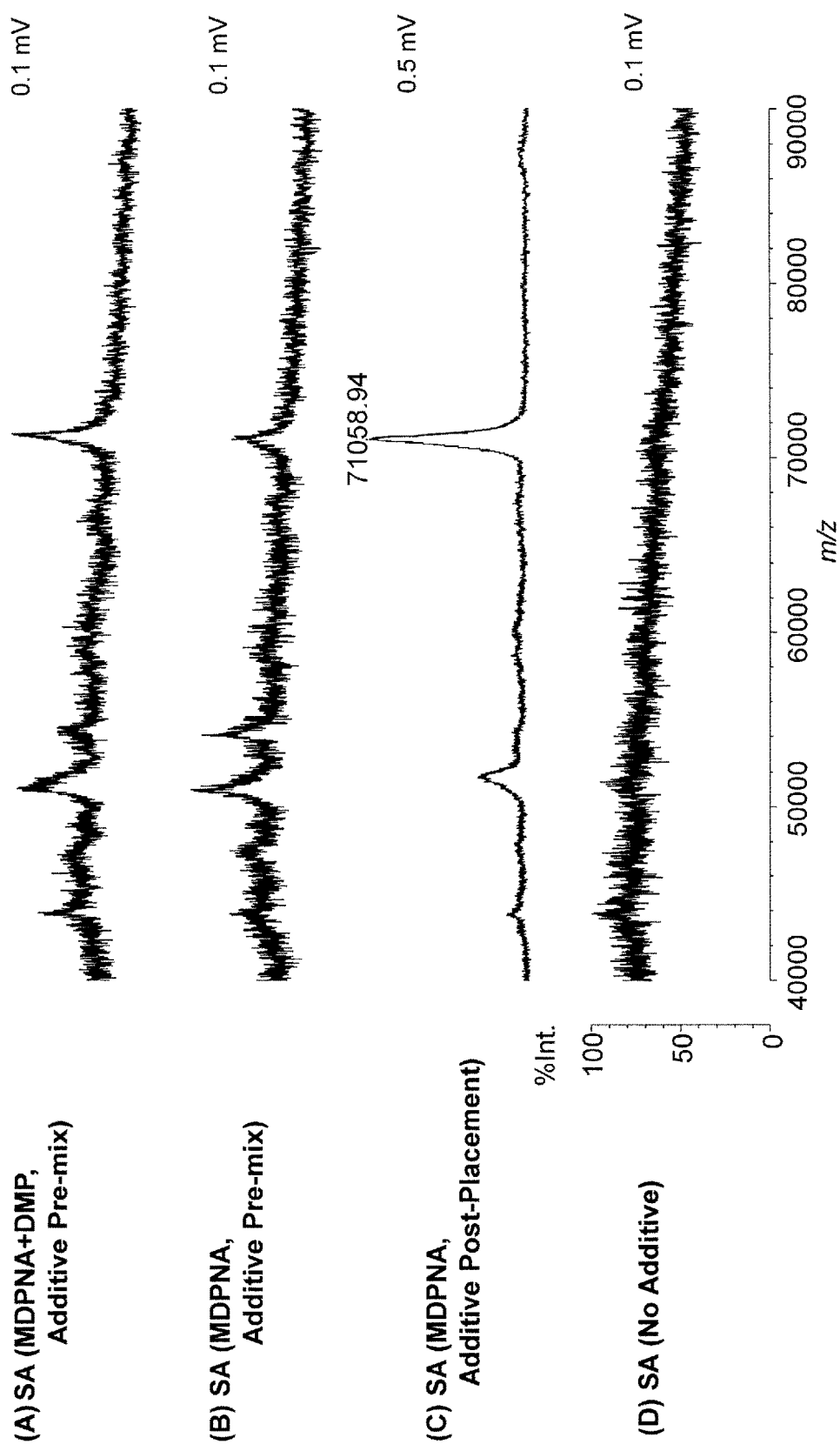

METHOD FOR ANALYZING MICROORGANISMS

TECHNICAL FIELD

The present invention relates to a method for analyzing microorganisms using a matrix assisted laser desorption/ionization mass spectrometer (MALDI-MS).

BACKGROUND ART

Matrix assisted laser desorption/ionization (MALDI), which is one of the ionization methods used in mass spectrometry, is a technique used for analyzing a substance which does not easily absorb laser light or a substance which is likely to undergo damage when irradiated with laser light, such as proteins. In this technique, the substance to be analyzed (which is hereinafter called the "target substance") is mixed with a matrix substance which easily absorbs laser light and easily turns into ions, and the mixture is irradiated with laser light to ionize the target substance. The matrix substance to be mixed with the target substance is normally prepared in the form of a solution. When mixed with the target substance, this matrix solution contains the target substance. The matrix solution in which the target substance has been contained is subsequently dried, whereby the solvent in the solution is vaporized and a crystal containing the target substance is formed. When this crystal is irradiated with laser light, the matrix substance absorbs the energy of the laser light and is rapidly heated to be eventually vaporized. Meanwhile, the target substance is also vaporized with the matrix substance. In this process, the target substance is ionized.

A mass spectrometer employing such a MALDI method (MALDI-MS) can be used for analyzing proteins or similar high-molecular compounds without significantly dissociating the compounds. The device is also suitable for the microanalysis of such compounds. Accordingly, in recent years, MALDI-MS has been widely used in the bioscience field.

For example, Patent Literature 1 discloses a method for identifying a microorganism based on a mass spectrum pattern obtained by a mass spectrometric analysis performed on a microorganism to be tested (which is hereinafter called the "test microorganism"). In this method, a solution to be tested, such as a solution containing proteins extracted from a test microorganism or the suspension of a test microorganism, is mixed with a matrix solution. The mixture is subsequently dried and subjected to an analysis with a MALDI-MS. The obtained mass spectrum pattern is compared with mass spectrum patterns of a large number of known microorganisms previously registered in a database (including the position, shape and other pieces of data concerning a "marker peak" of each microorganism, i.e. a peak which is characteristic of the microorganism) to identify the microorganism. Such a technique has been called "fingerprinting", since the technique utilizes a mass spectrum pattern as specific information to each microorganism (i.e. fingerprint).

It has been commonly known that an analysis with a MALDI-MS for a sample containing microorganisms has a low level of sensitivity within a high-mass range of mass-to-charge ratio m/z 15000 or higher, so that a mass spectrum within that mass range is rather unreliable and inaccurate. Therefore, if a marker peak that is useful for discriminating a microorganism to be identified is located within a high-mass range, the test microorganism cannot be correctly identified by fingerprinting.

There have been various approaches to the research and development for improving the sensitivity of MALDI-MS. One such conventional approach is the method in which an additional substance is added as a matrix additive when the mixed solution of a matrix and target substance is prepared by mixing the matrix solution and the target substance.

For example, Patent Literature 2 and Non Patent Literature 1 disclose that a phosphorylated peptide as an analysis target can be detected with a high level of sensitivity by adding methylenediphosphonic acid (MDPNA) as a matrix additive to 2,5-dihydroxybenzoic acid (DHB) as a matrix substance. In a method described in those documents, a sample is prepared by sequentially dropping a solution containing a phosphorylated peptide, a matrix additive solution, and a matrix solution in the mentioned order onto a sample plate, and subsequently drying the dropped solutions. This sample is analyzed with a MALDI-MS.

Non Patent Literature 2 and Non Patent Literature 3 disclose that using a surfactant as a matrix additive improves the sensitivity of a MALDI-MS analysis for a sample containing microorganisms. In a method described in these documents, a sample is prepared by applying a solution containing a test microorganism ("test microorganism solution") to a sample plate, dropping a surfactant onto the applied solution, and additionally dropping a matrix solution onto the test microorganism solution and the surfactant. The purpose of the use of the surfactant is to improve the solubility of the test microorganism.

CITATION LIST

Patent Literature

Patent Literature 1: JP 2015-184020A
Patent Literature 2: JP 2009-121857A

Non Patent Literature

Non Patent Literature 1: Rapid Commun. Mass Spectrom., 2008, Vol. 22, pp. 1109-1116
Non Patent Literature 2: J. Am. Soc. Mass. Spectrom., 2005, Vol. 16, pp. 1422-1426
Non Patent Literature 3: Rapid Commun. Mass Spectrom., 1999, Vol. 13, pp. 1067-1071

SUMMARY OF INVENTION

Technical Problem

In the method described in Patent Literature 2 as well as in the methods described in Non Patent Literature 1, 2 and 3, the solution containing a target substance, the matrix additive solution, and the matrix solution are individually dropped onto a sample plate by separate processes to prepare a sample. Such a sample preparation task is automatically performed by a sample preparation device or manually by an analysis operator. In any case, the task requires a considerable amount of time and labor.

Thus, in a method for analyzing a microorganism using a MALDI-MS, the problem to be solved by the present invention is to improve the sensitivity of an analysis without increasing the amount of time and labor required for the sample preparation. More specifically, the present invention is aimed at improving the sensitivity of an analysis within a high-mass range of m/z 15000 or higher within which the MALDI-MS analysis for a microorganism has a low level of sensitivity.

Solution to Problem

One aspect of the present invention developed for solving the previously described problem is a method for analyzing a microorganism using a matrix assisted laser desorption/ionization mass spectrometer (MALDI-MS), in which a matrix-and-additive mixture solution prepared beforehand by mixing one or both of an alkylphosphonic acid and a surfactant with a matrix substance is used in a process for matrix assisted laser desorption/ionization.

In the previously described method, either an alkylphosphonic acid or a surfactant, or both of them are used as matrix additives and are mixed with the matrix substance beforehand to prepare a matrix-and-additive mixture solution. After a solution which contains constituents of a microorganism to be analyzed has been dropped onto a sample plate, the matrix-and-additive mixture solution is dropped onto that solution and dried to form a mixed crystal which contains both the constituents of the microorganism and the matrix substance. This mixed crystal is used as the sample to be analyzed with a MALDI-MS. It is also possible to mix the solution containing the constituents of the microorganism with the matrix-and-additive mixture solution, drop the obtained mixed solution onto the sample plate, and dry the solution to obtain the sample. According to this method, the number of process steps for the sample preparation will be even fewer than in the case where the solution containing the constituents of the microorganism and the matrix-and-additive mixture solution are individually dropped by separate processes.

Alkylphosphonic acids can suppress the formation of alkaline metal adduct ions ($[M+Na]^+$, $[M+K]^+$, etc.) in an analysis of a protein-containing sample using a MALDI-MS. Examples of alkylphosphonic acids which contain one phosphonate group include phosphonic acid, methylphosphonic acid, phenylphosphonic acid, and 1-naphthylmethylphosphonic acid. Examples of alkylphosphonic acids which contain two phosphonate groups include methylenediphosphonic acid, ethylenediphosphonic acid, ethane-1-hydroxy-1,1-diphosphonic acid, nitrilotriphosphonic acid, and ethylenediaminetetraphosphonic acid. As a preferable mode of the present invention, methylenediphosphonic acid (MDPNA) can be used as the alkylphosphonic acid.

The surfactant is mainly used to improve the solubility of the constituents of the microorganism. Surfactants commonly used for extracting membrane proteins or other intracellular proteins can be used as the surfactant. A surfactant with which proteins can be extracted without denaturation may preferably be used. Examples of such a surfactant include decyl-β-D-maltopyranoside (DMP), N-decyl-β-D-maltopyranoside, N-octyl-β-D-glactopyranoside, N-dodecyl-β-D-maltoside and N-octyl-β-D-glucopyranoside, which are non-ionic surfactants, as well as N,N-dimethyldodecylamine-N-oxide and zwittergent 3-12, which are zwitterionic surfactants. As a preferable mode of the present invention, DMP can be used as the surfactant.

As the matrix substance, an appropriate substance can be selected according to the kind of microorganism to be analyzed and the identification level of the microorganism (e.g. family, genus, species, subspecies, pathotype, serotype or strain). Examples of such a matrix substance include sinapinic acid (SA), α-cyano-4-hydroxycinnamic acid (CHCA), and ferulic acid (FA). As a preferable mode of the present invention, SA can be used as the matrix substance. It has been commonly known that SA is useful for an analysis of proteins or similar high-mass molecules in a MALDI analysis.

In the previously described method for analyzing a microorganism, the matrix-and-additive mixture solution may preferably be prepared by dissolving the matrix substance at 10 to 30 mg/mL (preferably, 25 mg/mL), 0.1 to 5% (preferably, 1%) of MDPNA and 0.1 to 10 mM (preferably, 1 mM) of DMP in an aqueous solution containing 30 to 70% (preferably, 50%) of acetonitrile (ACN) and 0.1 to 3.0% (preferably, 0.6 to 1%) of trifluoroacetic acid (TFA). The kinds of preferable substances contained in the matrix-and-additive mixture solution as well as the preferable mixture ratio or concentration mentioned in this paragraph are based on general knowledge and experimental facts. It should be noted that the unit "%" as used in the present description means "percent by weight" unless otherwise specified.

Another method for analyzing a microorganism according to the present invention includes the steps of:

a) dropping either an ethanol solution containing 10 to 30 mg/mL sinapinic acid or a saturated ethanol solution of sinapinic acid onto a sample plate and drying the matrix solution;

b) preparing a matrix-microorganism mixture solution by mixing the matrix solution and a test microorganism; and c) additionally dropping the matrix-microorganism mixture solution onto a dried substance of the dropped ethanol solution or the dropped saturated ethanol solution on the sample plate, and drying the dropped matrix-and-additive mixture solution.

In any of the previously described methods for analyzing a microorganism according to the present invention, the method may include the steps of:

obtaining a mass spectrum for a sample containing a test microorganism, the mass spectrum covering a mass range including a high-mass range of m/z 10000 or higher in mass-to-charge ratio;

comparing the mass spectrum with mass-spectrum patterns stored in a database; and identifying the test microorganism based on a result obtained by comparing the mass spectrum with the mass-spectrum patterns.

Advantageous Effects of Invention

In a method for analyzing a microorganism according to the present invention, the use of one or both of an alkylphosphonic acid and a surfactant as a matrix additive in a process for analyzing a microorganism with a MALDI-MS enables high-sensitivity detection of the peaks originating from the microorganism. An experiment conducted by the present inventor confirmed that the sensitivity within a high-mass range of m/z 10000 or higher in mass-to-charge ratio in a mass spectrum is particularly improved by the previously described method.

Furthermore, according to the present invention, since the matrix additive is mixed with the matrix substance beforehand, the number of process steps for sample preparation on a sample plate is decreased. Accordingly, the amount of labor for sample preparation will be reduced, and the period of time for sample preparation will be shortened.

BRIEF DESCRIPTION OF DRAWINGS

FIG. 4B is a chart showing a mass-to-charge-ratio range of m/z 20000 to 33000 in the second set of mass specta obtained in the first example in which *Escherichia coli* (*E. coli* DH5α Electro-Cells) was used as the test microorganism, with each mass spectrum having a vertical axis which indicates relative intensities.

FIG. 6A is a chart showing a mass-to-charge-ratio range of m/z 20000 to 34000 in the mass spectra obtained in the second example in which *Salmonella enterica* (serotype: *Infantis*, jfrlSe 1402-4) was used as the test microorganism, with all mass spectra having the same intensity scale on their vertical axes.

FIG. 6C is a chart showing a mass-to-charge-ratio range of m/z 40000 to 90000 in the mass spectra obtained in the second example in which *Salmonella enterica* (serotype: *Infantis*, jfrlSe 1402-4) was used as the test microorganism, with each mass spectrum having a vertical axis which indicates relative intensities.

DESCRIPTION OF EMBODIMENTS

Figure 1:
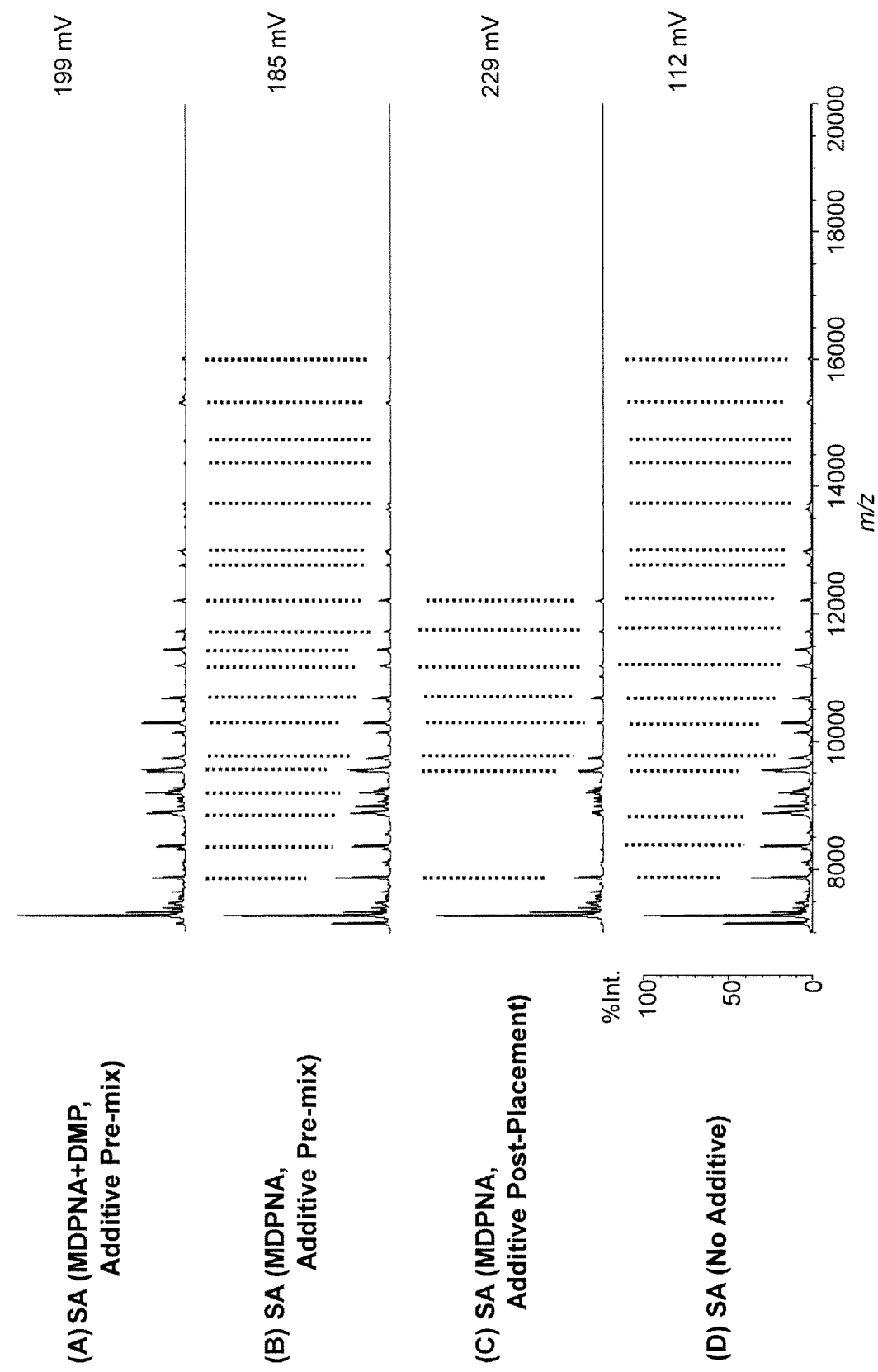
FIG. 1 is a chart showing a mass-to-charge-ratio range of m/z 7000 to 20000 in a first set of mass spectra obtained in the first example in which *Escherichia coli* (*E. coli* DH5α Electro-Cells) was used as the test microorganism.

In the method for analyzing a microorganism according to the present invention, a sample which contains constituents of a microorganism to be analyzed (which is hereinafter called the "test microorganism") is prepared. With this sample set in a MALDI-MS, a mass spectrometric analysis is performed to obtain a mass spectrum. The obtained mass spectrum is compared with mass-spectrum patterns stored in a database, whereby the kind of test microorganism (i.e. family, genus, species, subspecies, pathotype, serotype, strain or similar group to which the microorganism belongs) can be identified. As will be described later in detail, the method for analyzing a microorganism according to the present invention particularly allows for high-sensitivity acquisition of information concerning the molecular weight for a microorganism within a high-mass range of m/z 10000 or higher in mass-to-charge ratio in the obtained mass spectrum. This is suitable for identifying a microorganism for which a useful marker peak for the identification of the test microorganism is present within the high-mass range.

As the MALDI-MS, a MALDI time-of-flight mass spectrometer (MALDI-TOFMS) may preferably be used. MALDI-TOFMS can perform measurements over an extremely wide range of mass-to-charge ratios and yield mass spectra which are suitable for an analysis of high-mass molecules, such as proteins which constitute a microorganism.

The constituents of the test microorganism may be a cell extract or purified cell constituents, such as ribosomal proteins, obtained from the cell extract. Fungus bodies or cell suspension may also be directly used in their original form.

In the method for analyzing a microorganism according to the present invention, a matrix-and-additive mixture solution is prepared by mixing an alkylphosphonic acid or/and a surfactant as matrix additives with the matrix substance beforehand. This matrix-and-additive mixture solution is used for the preparation of samples for MALDI-MS analysis.

The matrix-and-additive mixture solution is obtained by dissolving one or both of the alkylphosphonic acid and the surfactant, and the matrix substance, in a solvent so that the concentrations of these substances become their respective specified values. It is also possible to initially prepare a matrix solution (by dissolving a matrix substance in a solvent) and a matrix additive solution (by dissolving a matrix additive in a solvent), and subsequently mix these two solutions to obtain the matrix-and-additive mixture solution.

The use of an alkylphosphonic acid as the matrix additive added to the matrix-and-additive mixture solution has the effect of suppressing the formation of alkaline metal adduct ions. This suppresses the detection of the peaks of the alkaline metal adduct ions which form background noise in the mass spectrum. Consequently, it is expected the peaks originating from the constituents of the microorganism will be more easily observed, and the detection sensitivity for the peaks originating from the constituents of the microorganism will be improved.

The use of a surfactant as the matrix additive added to the matrix-and-additive mixture solution is likely to improve the solubility of the test microorganism when a solution containing the constituents of the test microorganism (sample solution) is mixed with the matrix-and-additive mixture solution. Therefore, it is expected that the peaks of a sample which is barely soluble and has been difficult to analyze will be more satisfactorily detected.

Examples of the solvents that can be used for the matrix-and-additive mixture solution include a mixed solution of water and acetonitrile (ACN) as well as a mixed solution obtained by adding an organic acid, such as a trifluoroacetic acid (TFA), trichloroacetic acid or acetic acid, to the mixed solution of water and ACN. It is expected that the addition of the organic acid to the solvent of the matrix-and-additive mixture solution will lead to high-sensitivity detection of the peak of a protonated molecule of the test microorganism ([M+H]$^+$) or related ion.

After a test microorganism is applied to a sample plate, or after a solution containing constituents of the test microorganism is dropped onto the sample plate, the matrix-and-additive mixture solution is additionally dropped onto it and dried. Consequently, a mixed crystal of the constituents of the test microorganism and the matrix is obtained. This mixed crystal is used as the sample for the MALDI-MS analysis. Unlike the conventional method in which a matrix solution and an additive solution are mixed together by being sequentially and individually dropped onto a sample plate, the mixed solution of the matrix substance and the additive in the present invention is prepared beforehand, so that fewer process steps are required to drop solutions onto a sample plate. It is also possible to mix the matrix-and-additive mixture solution with the constituents of the test microorganism beforehand, drop the mixture onto the sample plate, and dry the dropped solution to obtain the mixed crystal. In this case, the number of process steps for sample preparation on the sample plate will be even further decreased.

Hereinafter, the method for analyzing a microorganism according to the present invention is described by means of examples. It should be noted that the following examples are merely illustrative and should not be construed as limiting the present invention. In particular, the kinds of substances contained in the various solutions used in the following examples, such as the matrix solution, matrix-and-additive mixture solution and additive solution, as well as the mixture ratio and concentration of each substance are mere examples and can be changed or varied within controllable ranges based on the common knowledge of a person skilled in the art. It is expected that any change or variation which falls within such a range will produce similar effects to those described in the following examples.

In the following examples, samples which had been prepared by a method for analyzing a microorganism according to the present invention were analyzed with a MALDI-MS. In order to confirm the effects of those samples, additional samples were also prepared by two methods different from the present invention and analyzed with the MALDI-MS.

As will be described later in detail, in the present invention, a matrix solution in which a matrix additive is mixed beforehand ("matrix-and-additive mixture solution") is used for sample preparation. For example, after a matrix-and-additive mixture solution has been prepared, the matrix-and-additive mixture solution is mixed with a test microorganism beforehand, and the obtained solution is dropped onto a sample plate to obtain a sample. This method is hereinafter called the "additive pre-mix method".

One of the two methods different from the present invention is a method in which a mixed solution of the matrix substance and the test microorganism is dropped onto a sample plate, and a matrix additive solution is additionally dropped onto the mixed solution to obtain a sample. This method is hereinafter called the "additive post-placement method".

The other one of the two different methods is a method in which no matrix additive is used, and only the matrix solution is used for sample preparation. This method is hereinafter called the "no-additive method".

FIRST EXAMPLE

<1. Test Microorganism>

As the test microorganism, a commercially available *Escherichia coli* (*E. coli* DH5α Electro-Cells, Product Code: TKR 9027, manufactured by Takara Bio Inc.) was used. *E. coli* DH5α Electro-Cells is a solution containing *E. coli* DH5α strain. This solution is hereinafter called the "test microorganism solution".

<2-1. Preparation of Matrix Solution>

Sinapinic acid (SA, manufactured by Wako Pure Chemical Industries, Ltd.) was dissolved in an aqueous solution containing 50% acetonitrile (ACN) and 0.6% trifluoroacetic acid (TFA) solution to obtain a matrix solution containing 25 mg/mL sinapinic acid. This matrix solution is hereinafter labeled "SA-2".

<2-2. Preparation of Matrix-and-Additive Mixture Solutions>

In the present example, three kinds of matrix-and-additive mixture solution were prepared as follows:

(1) SA and methylenediphosphonic acid (MDPNA) were dissolved in an aqueous solution containing 50% ACN and 0.6% TFA solution to obtain a matrix-and-additive mixture solution containing 25 mg/mL SA and 1% (percent by weight; the same applies to the following descriptions) MDPNA. This matrix-and-additive mixture solution is hereinafter labeled "SA-3".

(2) SA and decyl-β-D-maltopyranoside (DMP) were dissolved in an aqueous solution containing 50% ACN and 0.6% TFA solution to obtain a matrix-and-additive mixture solution containing 25 mg/mL SA and 1 mM DMP. This matrix-and-additive mixture solution is hereinafter labeled "SA-4".

(3) SA, MDPNA and DMP were dissolved in an aqueous solution containing 50% ACN and 0.6% TFA solution to obtain a matrix-and-additive mixture solution containing 25 mg/mL SA, 1% MDPNA and 1 mM DMP. This matrix-and-additive mixture solution is hereinafter labeled "SA-5".

<2-3. Preparation of Additive Solution>

In the present example, two kinds of additive solutions were prepared as follows:

(1) MDPNA was dissolved in an aqueous solution containing 50% ACN and 0.6% TFA solution to obtain an additive solution containing 1% MDPNA. This additive solution is hereinafter labeled "A-1".

(2) DMP was dissolved in an aqueous solution containing 50% ACN and 0.6% TFA solution to obtain an additive solution containing 1 mM DMP. This additive solution is hereinafter labeled "A-2".

<3. Mass Spectrometric Analysis>

A MALDI time-of-flight mass spectrometer (MALDI-TOFMS, manufactured by Shimadzu Corporation under the trade name of AXIMA-Performance) was used for the analysis of the samples. The measurement was performed in the linear mode (positive ion mode). All data were acquired by "raster analysis". Raster analysis is an automatic measurement function provided in the aforementioned mass spectrometer, in which mass spectrum data is acquired for each of the samples in the wells on a sample plate by delivering a specified number of shots of laser beam onto each of the specified number of points on the sample. In the present example, the data-collecting task including the steps of delivering the laser beam onto four wells (n=4) on the sample plate and acquiring mass spectrum data was performed multiple times for each of a plurality of test microorganisms.

<4. Preparation of Samples>

<4-1. Preparation of Sample by Additive Pre-mix Method>

(1) Initially, the test microorganism solution was 50-fold diluted with each of the three matrix-and-additive mixture solutions SA-3, SA-4 and SA-5 to obtain three kinds of matrix-additive-microorganism mixture solutions.

(2) Next, for each of the three matrix-additive-microorganism mixture solutions, 1 μL of the solution was dropped onto the wells on one sample plate.

(3) Subsequently, the matrix-additive-microorganism mixture solution in the wells of each sample plate was dried, and the obtained crystal of the matrix-microorganism mixture was used as a sample.

<4-2. Preparation of Samples by Additive Post-Placement Method>

(1) Initially, the test microorganism solution was 50-fold diluted with the matrix solution SA-2 to obtain a matrix-microorganism mixture solution.

(2) Next, 1 μL of the matrix-microorganism mixture solution was dropped onto each of the wells on a sample plate and dried.

(3) Subsequently, 1 μL of the additive solution A-1 was dropped onto each of the dried matrix-microorganism mixture solutions in the wells on one sample plate, while 1 μL of the additive solution A-2 was dropped onto each of the dried matrix-microorganism mixtures in the wells on another sample plate. Then, the dropped solutions on both sample plates were dried, and the obtained crystal of the matrix-microorganism mixture was used as a sample.

<4-3. Preparation of Samples by No-Additive Method>

(1) Initially, the test microorganism solution was 50-fold diluted with the matrix solution SA-2 to obtain a matrix-microorganism mixture solution.

(2) Next, 1 μL of the matrix-microorganism mixture solution was dropped onto each of the wells on the sample plate.

(3) Subsequently, the matrix-microorganism mixture solution in the wells was dried, and the obtained crystal of the matrix-microorganism mixture was used as a sample.

The previously described sample-preparing tasks may be manually performed by an operator, or an automatic dropping device may be used. The solution dropped into the wells on the sample plate may be naturally dried, or warm air may be supplied to dry it.

<5. Results>

FIGS. 1, 2, 3, 4A and 4B show mass spectra obtained in the first example.

Figure 2:
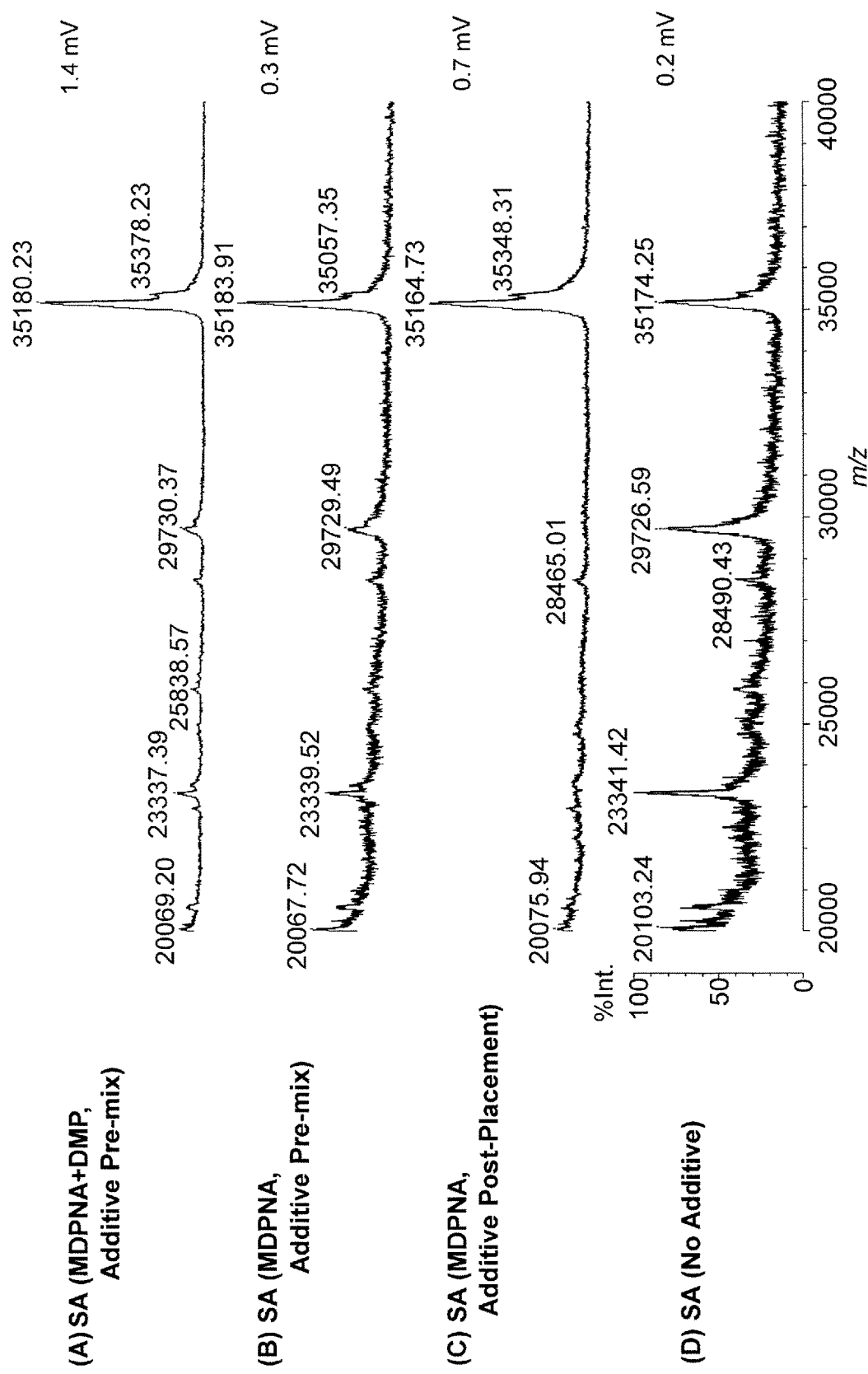
FIG. 2 is a chart showing a mass-to-charge-ratio range of m/z 20000 to 40000 in the first set of mass spectra obtained in the first example in which *Escherichia coli* (*E. coli* DH5α Electro-Cells) was used as the test microorganism.

Charts (A) and (B) in each of FIGS. 1 and 2 are mass spectra obtained for samples prepared by the additive pre-mix methods in which SA-5 and SA-3 were respectively used as the matrix-and-additive mixture solution. Chart (C) in each of FIGS. 1 and 2 is a mass spectrum obtained for a sample prepared by the additive post-placement method in which the matrix additive solution A-1 was used. Chart (D) in each of FIGS. 1 and 2 is a mass spectrum obtained for a sample prepared by the no-additive method. FIG. 1 shows the mass spectra within a mass-to-charge-ratio range of m/z 7000 to 20000. FIG. 2 shows the mass spectra within a mass-to-charge-ratio range of m/z 20000 to 40000.

As shown in FIG. 1, within the mass-to-charge-ratio range of m/z 7000 to 20000, the mass spectrum (C) obtained by the additive post-placement method exhibited a slightly different peak profile from the mass spectrum (D) obtained by the no-additive method. By comparison, the mass spectra (A) and (B) obtained by the additive pre-mix methods both exhibited almost the same peak profile as the mass spectrum (D) obtained by the no-additive method.

Furthermore, as shown in FIG. 2, within the mass-to-charge-ratio range of m/z 20000 to 40000, an improvement in the peak intensity or signal-to-noise ratio was confirmed in the mass spectrum (C) obtained by the additive post-placement method as well as the mass spectrum (A) and (B) obtained by the additive pre-mix methods as compared to the mass spectrum (D) obtained by the no-additive method. In particular, in the mass spectrum (A) of the sample prepared by the additive pre-mix method using the matrix-and-additive mixture solution SA-5 in which both MDPNA and DMP as the matrix additives were mixed with the matrix substance, the background noise within the high-mass range was reduced, and the peaks were detected with a high level of sensitivity.

Figure 3:
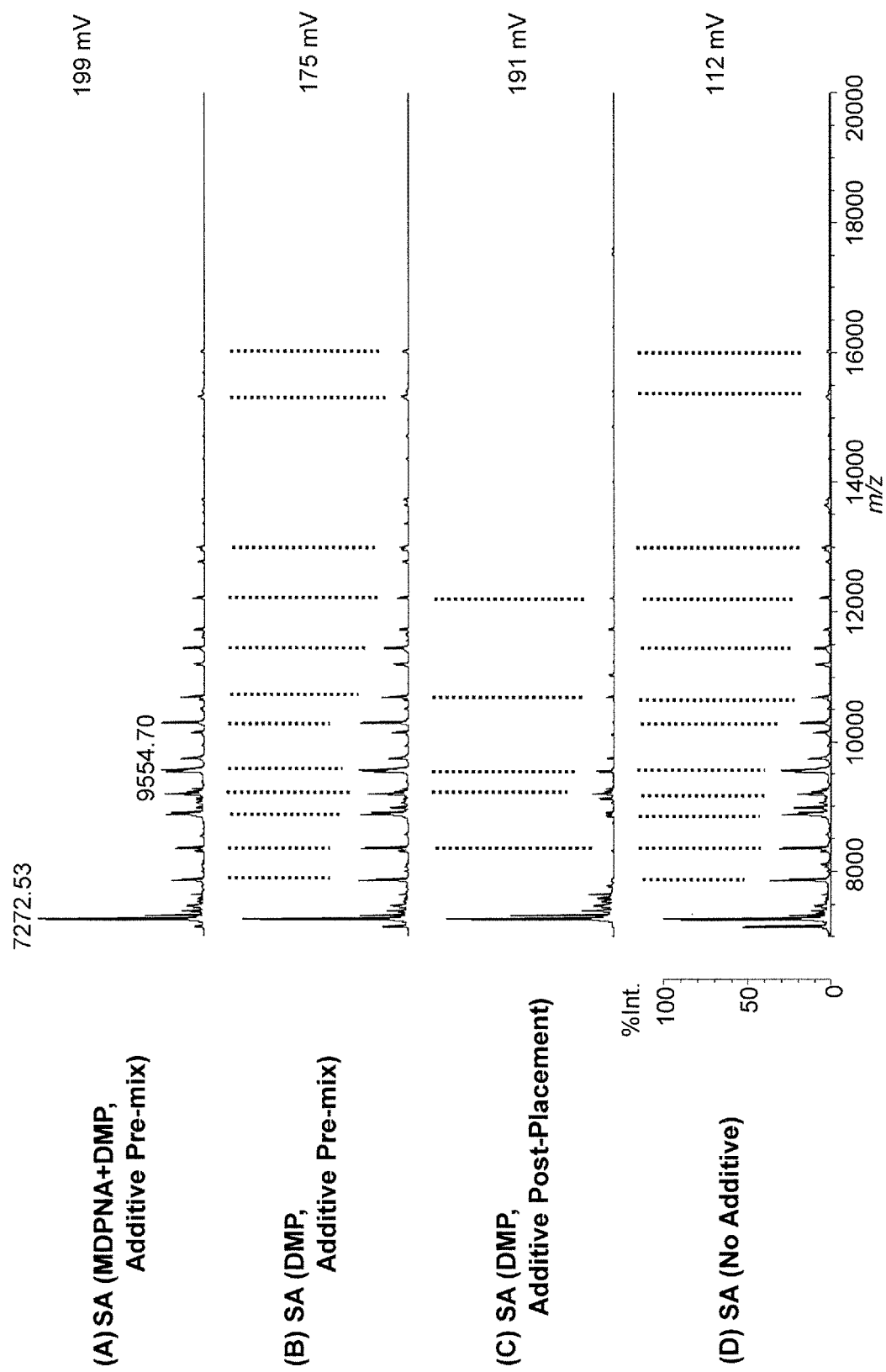
FIG. 3 is a chart showing a mass-to-charge-ratio range of m/z 7000 to 20000 in a second set mass spectra obtained in the first example in which *Escherichia coli* (*E. coli* DH5α Electro-Cells) was used as the test microorganism.
Figure 4A:
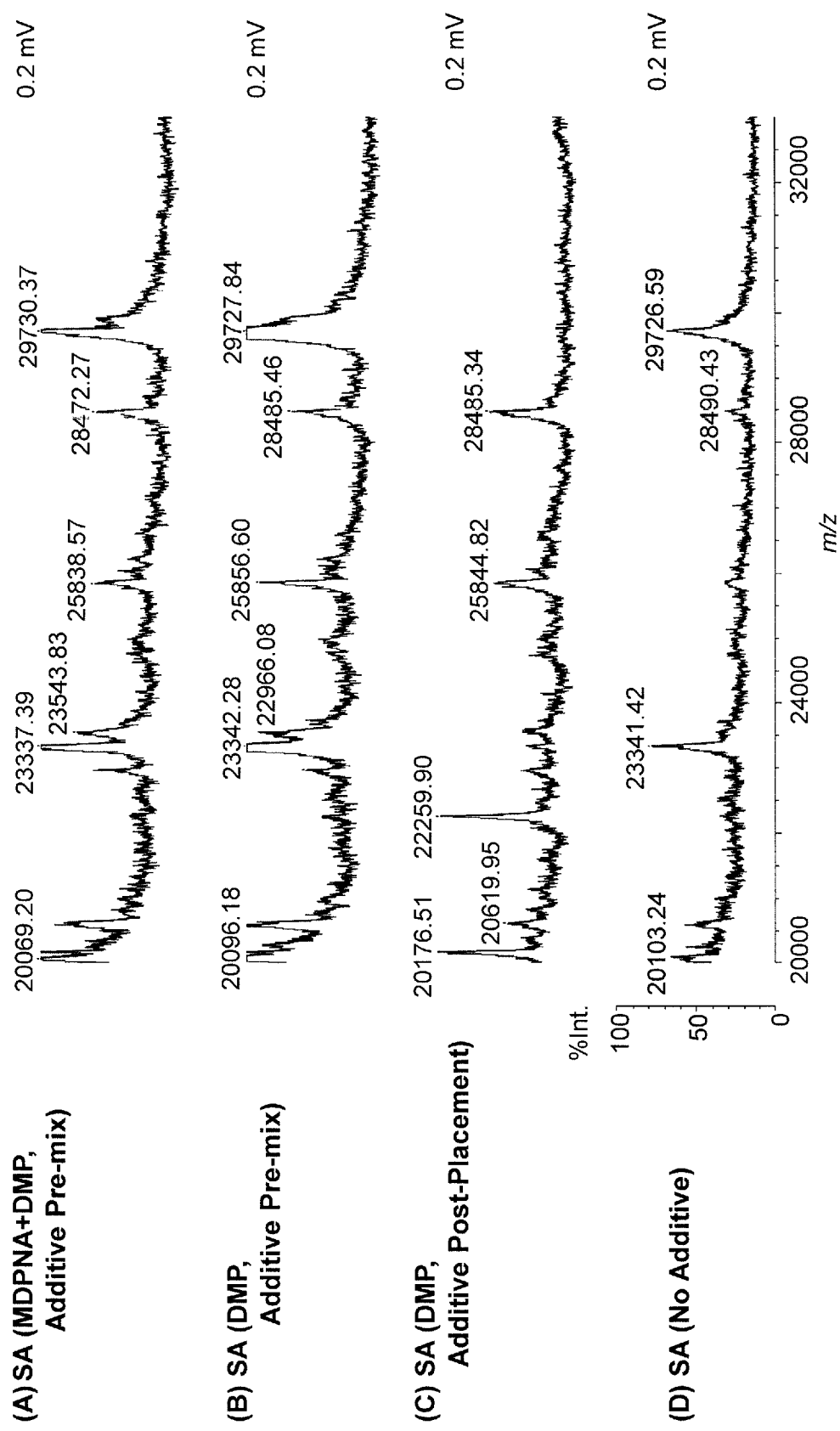
FIG. 4A is a chart showing a mass-to-charge-ratio range of m/z 20000 to 33000 in the second set of mass spectra obtained in the first example in which *Escherichia coli* (*E. coli* DH5α Electro-Cells) was used as the test microorganism, with all mass spectra having the same intensity scale on their vertical axes.

Charts (A) and (B) in each of FIGS. 3, 4A and 4B are mass spectra obtained for samples prepared by the additive pre-mix methods in which SA-5 and SA-4 were respectively used as the matrix-and-additive mixture solution. Chart (C) in each of FIGS. 3, 4A and 4B is a mass spectrum obtained for a sample prepared by the additive post-placement method in which the matrix additive solution A-2 was used. Chart (D) in each of FIGS. 3, 4A and 4B is a mass spectrum obtained for a sample prepared by the no-additive method.

FIG. 3 shows the mass spectra within a mass-to-charge-ratio range of m/z 7000 to 20000. FIGS. 4A and 4B each show the mass spectra within a mass-to-charge-ratio range of m/z 20000 to 33000. It should be noted that all charts (A) to (D) in FIG. 4A have the same intensity scale on the vertical axis, whereas the scales on the vertical axes of charts (A) to (D) in FIG. 4B are adjusted to show the peak heights in relative intensity in a similar manner to the other data so as to allow for the comparison of peak profiles.

As shown in FIG. 3, within the mass-to-charge-ratio range of m/z 7000 to 20000, the mass spectrum (C) obtained by the additive post-placement method exhibited a slightly different peak profile from the mass spectrum (D) obtained by the no-additive method. By comparison, the mass spectra (A) and (B) obtained by the additive pre-mix methods both exhibited almost the same peak profile as the mass spectrum (D) obtained by the no-additive method, regardless of whether SA-5 or SA-4 was used as the matrix-and-additive mixture solution.

Furthermore, as shown in FIGS. 4A and 4B, within the mass-to-charge-ratio range of m/z 20000 to 33000, the mass spectra (A) and (B) obtained by the additive pre-mix methods both exhibited almost the same peak profile as the mass spectrum (D) obtained by the no-additive method. Additionally, some peaks which did not appear on the mass spectrum (D) obtained by the no-additive method were observed in the mass spectra (A) and (B). Thus, an improvement in the peak intensity or signal-to-noise ratio was confirmed.

The results described thus far demonstrate that the sample preparation by the additive pre-mix method is particularly effective for improving the sensitivity within a high-mass range. Since the improvement of the sensitivity is achieved without any change in the peak profile, there is no loss of peaks due to the suppression effect caused by a change in the order of peak intensity or other factors. This consequently produces favorable effects. For example, the self-calibration peaks which have been used before the addition of the additive can be continuously used as they are, and the target peaks designated before the addition of the additive can be certainly detected with the improved sensitivity. Furthermore, as compared to the additive post-placement method, the additive pre-mix method expedites an analysis of a sample since the number of process steps for dropping solutions onto a sample plate is the same as in the no-additive method.

SECOND EXAMPLE

<1. Test Microorganism>

*Salmonella enterica* (serotype: *Infantis*, jfrlSe 1402-4) isolated from a field isolate and cultured on LB agar at 37 degrees Celsius for 20 hours was used as the test microorganism.

<2-1. Preparation of Matrix Solution>

A (saturated) matrix solution was prepared by dissolving sinapinic acid (SA) in an ethanol solution to a content of 25 mg/mL This matrix solution is hereinafter labeled "SA-1".

Additionally, the matrix solution SA-2 was prepared using the same solvent and matrix substance as in the first example.

<2-2. Preparation of Matrix-and-Additive Mixture Solutions>

The three kinds of matrix-and-additive mixture solutions SA-3, SA-4 and SA-5 were prepared using the same combinations of the solvent and matrix substances as in the first example.

<2-3. Preparation of Additive Solution>

The additive solution A-1 was prepared using the same combination of the solvent and matrix additive as in the first example.

<3. Mass Spectrometric Analysis>

For the analysis of the samples, as in the first example, the MALDI time-of-flight mass spectrometer (MALDI-TOFMS, manufactured by Shimadzu Corporation under the trade name of AXIMA-Performance) operated in the linear mode (positive ion mode) was used, and the same method was used to acquire data.

<4. Preparation of Samples>

<4-1. Preparation of Sample by Additive Pre-mix Method>

(1) Initially, an amount of test microorganism corresponding to a few colonies was put in 10 μL of each of the three kinds of matrix-and-additive mixture solutions SA-3 to SA-5 to obtain sample suspensions of SA-3 to SA-5.

(2) Next, 0.5 μL of the matrix solution SA-1 was dropped in each well on a sample plate and dried. Then, one of the three sample suspensions of SA-3 to SA-5 (1.2 μL) was dropped onto the dried substance.

(3) Subsequently, the sample suspension of SA-3, SA-4 or SA-5 in the wells on the sample plate was dried, and the obtained crystal of the matrix-microorganism mixture was used as a sample.

<4-2. Preparation of Samples by Additive Post-Placement Method>

(1) Initially, an amount of test microorganism corresponding to a few colonies was put in 10 μL of the matrix solution SA-2 to obtain a sample suspension of SA-2.

(2) Next, 0.5 μL of the matrix solution SA-1 was dropped onto each well on a sample plate and dried. Then, 1.2 μL of the sample suspension of SA-2 was additionally dropped onto the dried substance.

(3) Subsequently, the sample suspension of SA-2 in the wells on the sample plate was dried. Then, 1 μL of the additive solution A-1 was dropped onto the dried substance and dried.

(4) The crystal of the matrix-microorganism mixture obtained in (3) was used as a sample.

<4-3. Preparation of Samples by No-Additive Method>

(1) Initially, an amount of test microorganism corresponding to a few colonies was put in 10 μL of the matrix solution SA-2 to obtain a sample suspension of SA-2.

(2) Next, 0.5 μL of the matrix solution SA-1 was dropped into each well on a sample plate and dried. Then, 1.2 μL of the sample suspension of SA-2 was additionally dropped onto the dried substance.

(3) Subsequently, the sample suspension of SA-2 in the wells was dried, and the obtained crystal of the matrix-microorganism mixture was used as a sample.

<5. Results>

FIGS. 5 to 9 show mass spectra obtained in the second example.

Figure 5:
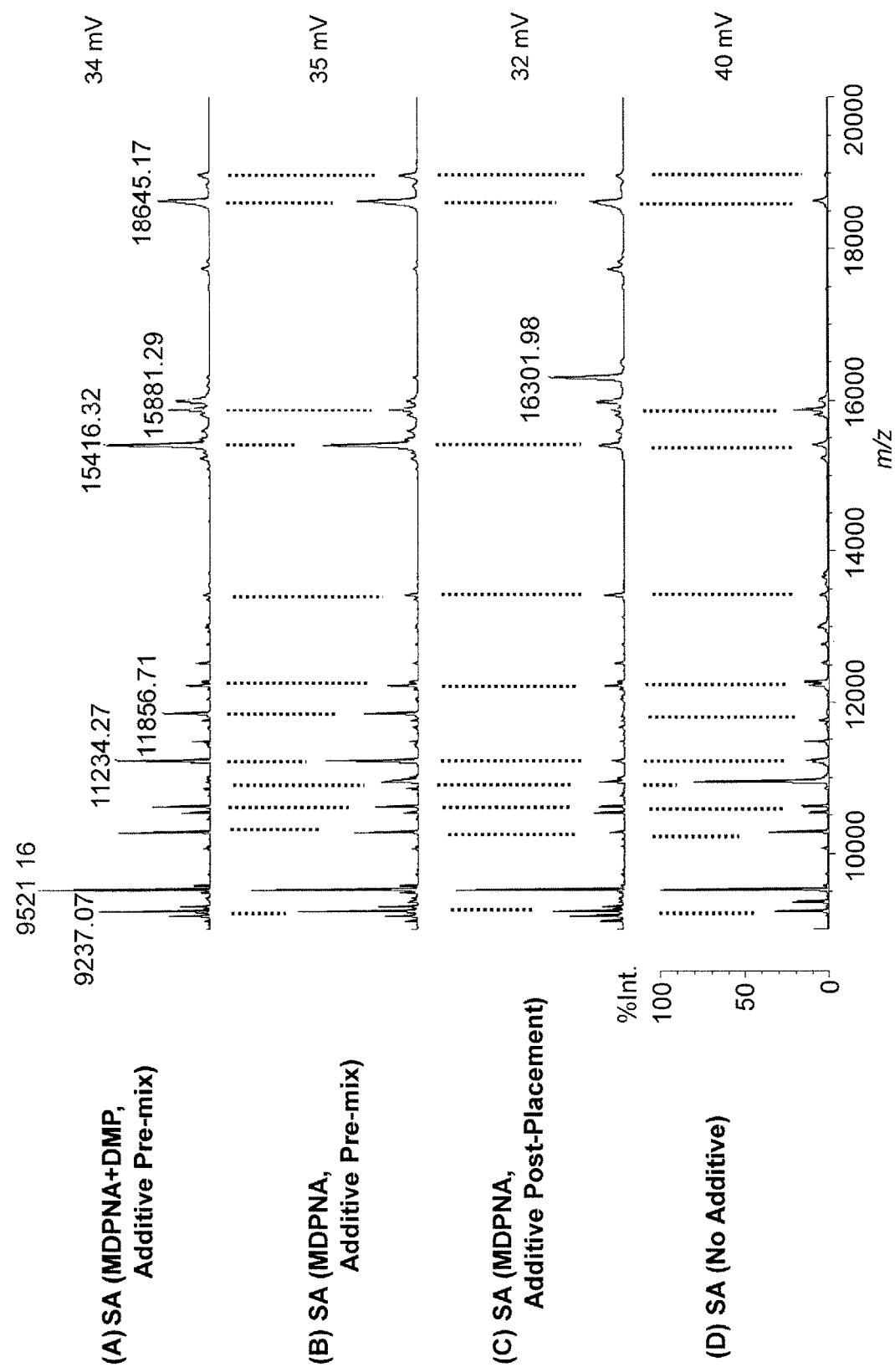
FIG. 5 is a chart showing a mass-to-charge-ratio range of m/z 9000 to 20000 in mass spectra obtained in the second example in which *Salmonella enterica* (serotype: *Infantis*, jfrlSe 1402-4) was used as the test microorganism.
Figure 6B:
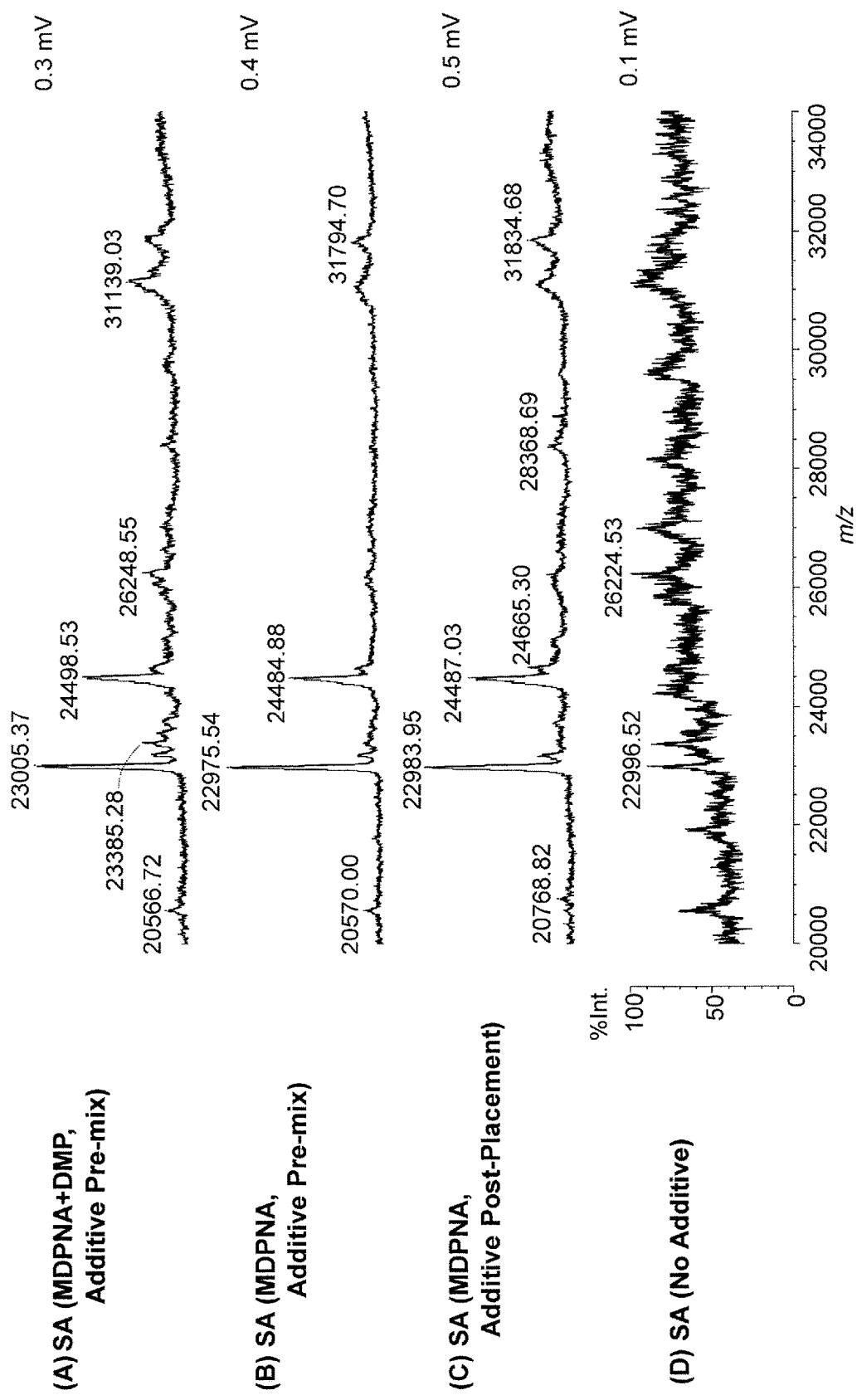
FIG. 6B is a chart showing a mass-to-charge-ratio range of m/z 20000 to 34000 in the mass spectra obtained in the second example in which *Salmonella enterica* (serotype: *Infantis*, jfrlSe 1402-4) was used as the test microorganism, with each mass spectrum having a vertical axis which indicates relative intensities.

Charts (A) and (B) in each of FIGS. 5, 6A, 6B and 6C are mass spectra obtained for samples prepared by the additive pre-mix methods in which SA-5 and SA-3 were respectively used as the matrix-and-additive mixture solution. Chart (C) in each of FIGS. 5, 6A, 6B and 6C is a mass spectrum obtained for a sample prepared by the additive post-placement method. Chart (D) in each of FIGS. 5, 6A, 6B and 6C is a mass spectrum obtained for a sample prepared by the no-additive method. FIG. 5 shows the mass spectra within a mass-to-charge-ratio range of m/z 9000 to 20000. FIGS. 6A and 6B each show the mass spectra within a mass-to-charge-ratio range of m/z 20000 to 34000. FIG. 6C shows the mass spectra within a mass-to-charge-ratio range of m/z 40000 to 90000.

As shown in FIG. 5, within the mass-to-charge-ratio range of m/z 9000 to 20000, the mass spectrum (C) obtained by the additive post-placement method exhibited a slightly different peak profile from the mass spectrum (D) obtained by the no-additive method. By comparison, the mass spectra (A) and (B) obtained by the additive pre-mix methods both exhibited almost the same peak profile as the mass spectrum (D) obtained by the no-additive method.

Within the mass-to-charge-ratio range of m/z 20000 to 34000 shown in FIGS. 6A and 6B, an improvement in the peak intensity or signal-to-noise ratio was confirmed in the mass spectra (A) to (C) obtained by the additive pre-mix methods and the additive post-placement method as compared to the mass spectrum (D) obtained by the no-additive method.

Similarly, within the high-mass range of m/z 40000 to 90000 in mass-to-charge ratio shown in FIG. 6C, an improvement in the peak intensity or signal-to-noise ratio was confirmed in the mass spectra (A) to (C) obtained by the additive pre-mix methods and the additive post-placement method as compared to the mass spectrum (D) obtained by the no-additive method. In particular, within a high-mass range of m/z 40000 or higher in mass-to-charge-ratio, the peaks were detected with high sensitivity by the additive post-placement method. It should be noted that the number of process steps for dropping in the preparation of samples by the additive pre-mix method is the same as in the no-additive method.

Figure 7:
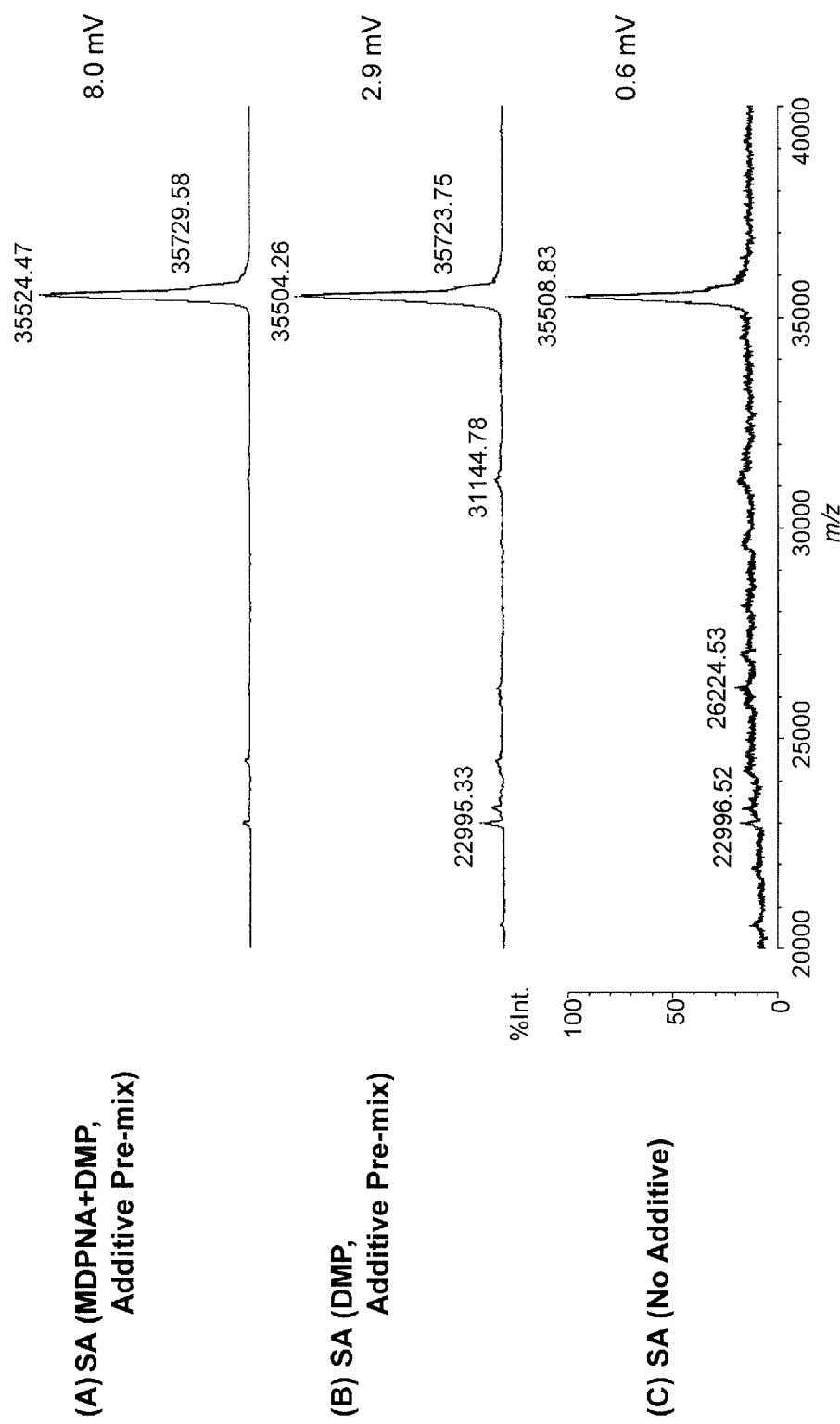
FIG. 7 is a chart showing a mass-to-charge-ratio range of m/z 20000 to 40000 in the mass spectra obtained in the second example in which *Salmonella enterica* (serotype: *Infantis*, jfrlSe 1402-4) was used as the test microorganism.
Figure 8:
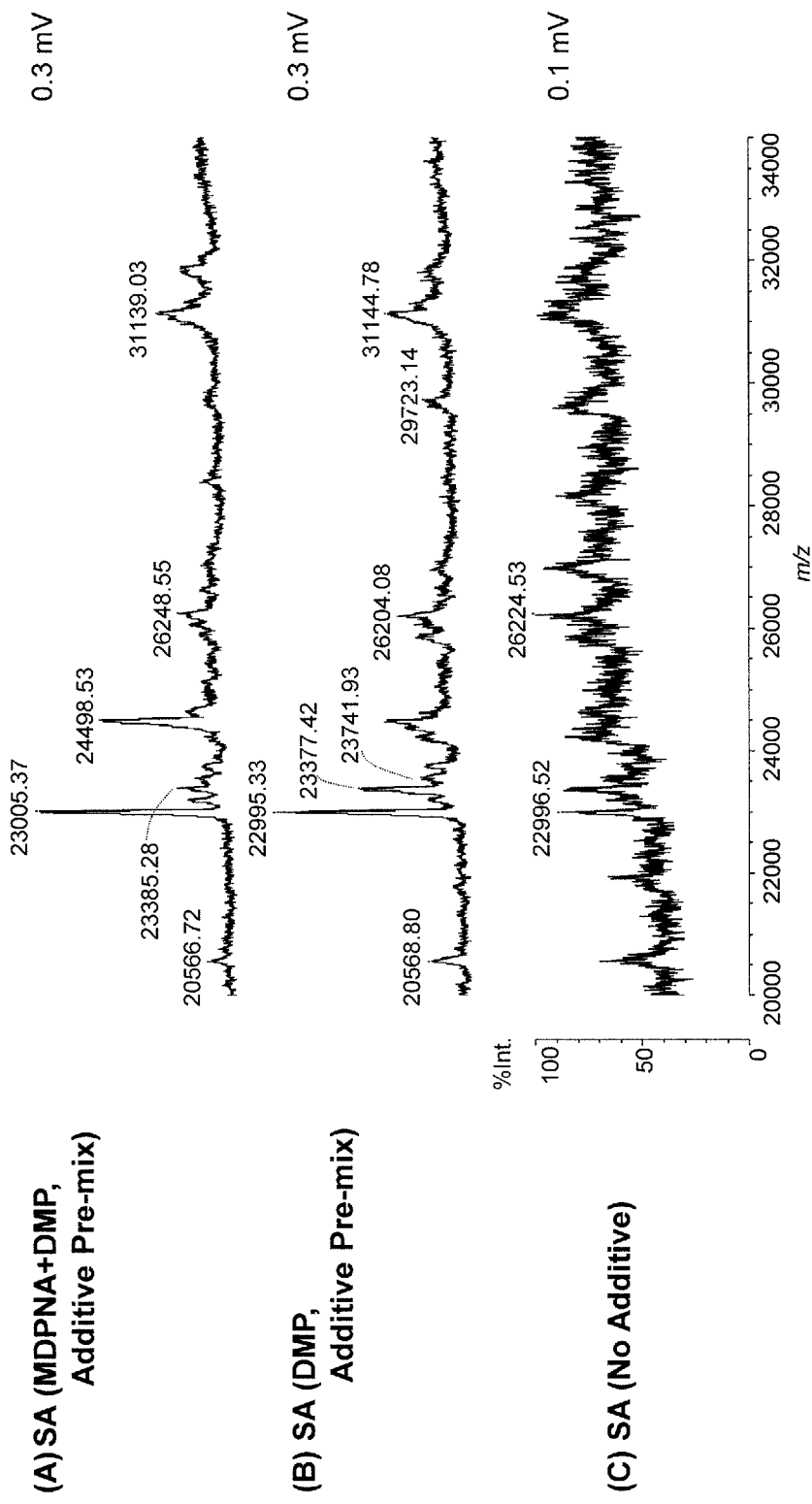
FIG. 8 is a chart showing a mass-to-charge-ratio range of m/z 20000 to 34000 in the mass spectra obtained in the second example in which *Salmonella enterica* (serotype: *Infantis*, jfrlSe 1402-4) was used as the test microorganism.
Figure 9:
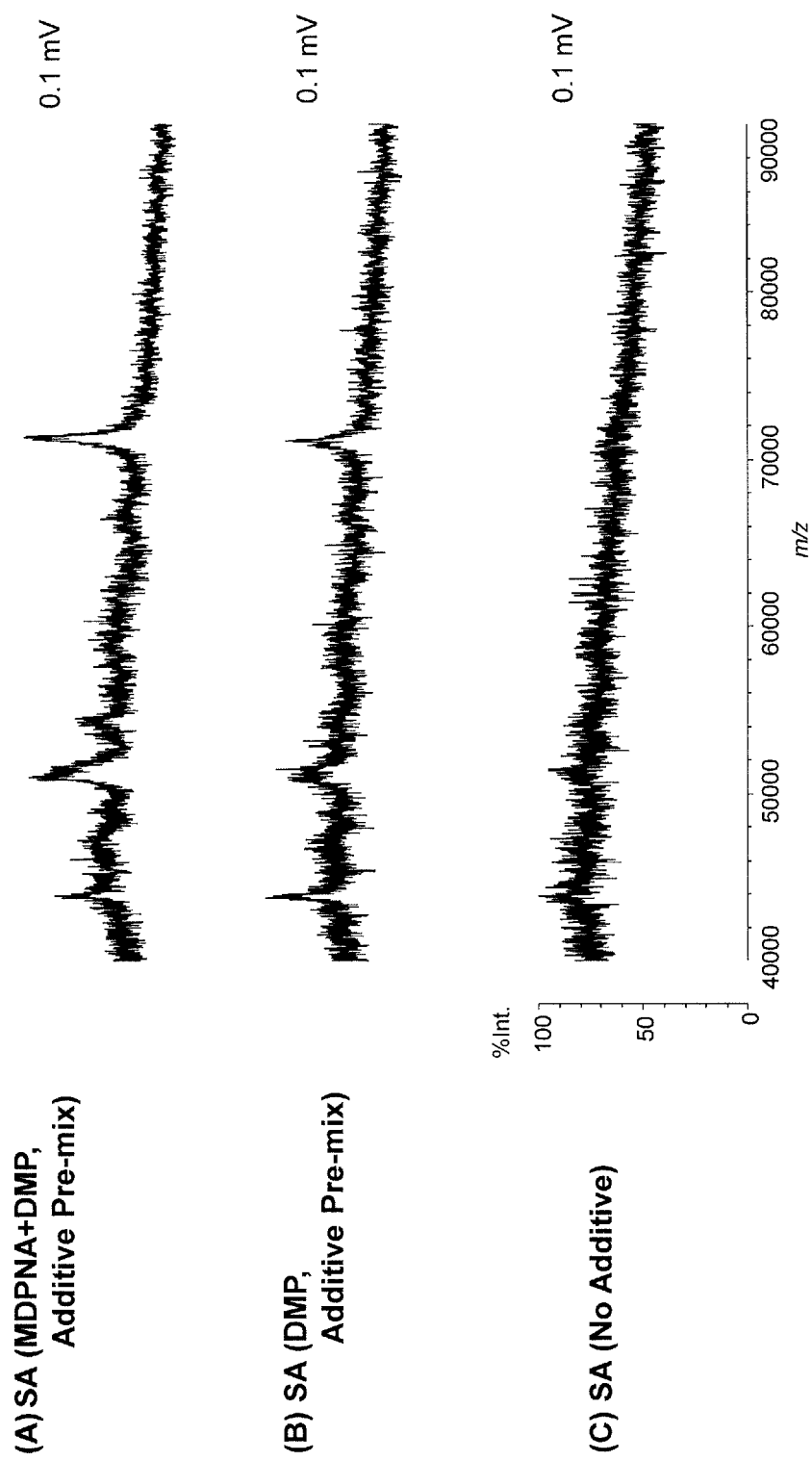
FIG. 9 is a chart showing a mass-to-charge-ratio range of m/z 40000 to 90000 in the mass spectra obtained in the second example in which *Salmonella enterica* (serotype: *Infantis*, jfrlSe 1402-4) was used as the test microorganism.

Charts (A) and (B) in each of FIGS. 7 to 9 are mass spectra obtained for samples prepared by the additive pre-mix methods in which SA-5 and SA-4 were respectively used as the matrix-and-additive mixture solution. Chart (C) in each of FIGS. 7 to 9 is a mass spectrum obtained for a sample prepared by the no-additive method. FIG. 7 shows the mass spectra within a mass-to-charge-ratio range of m/z 20000 to 40000. FIG. 8 shows the mass spectra within a mass-to-charge-ratio range of m/z 20000 to 34000. FIG. 9 shows the mass spectra within a mass-to-charge-ratio range of m/z 40000 to 90000.

As shown in FIG. 7, within the mass-to-charge-ratio range of m/z 20000 to 40000, the mass spectra (A) and (B) obtained by the additive pre-mix methods both exhibited the same peak profile as the mass spectrum (C) obtained by the no-additive method.

Furthermore, within the mass-to-charge-ratio range of m/z 20000 to 34000 shown in FIG. 8 as well as the mass-to-charge-ratio range of m/z 40000 to 90000 shown in FIG. 9, an improvement in the peak intensity or signal-to-noise ratio was confirmed in the mass spectra (A) and (B) obtained by the additive pre-mix method as compared to the mass spectrum (C) obtained by the no-additive method. In particular, within a high-mass range of m/z 20000 or higher in mass-to-charge ratio, the peaks were detected with high sensitivity by the additive pre-mix method.

The results described thus far demonstrate that the sample preparation by the additive pre-mix method is particularly effective for improving the sensitivity within a high-mass range. Since the improvement of the sensitivity is achieved without any change in the peak profile, there is no loss of peaks due to the suppression effect caused by a change in the order of peak intensity or other factors. This consequently produces favorable effects. For example, the self-calibration peaks which have been used before the addition of the additive can be continuously used as they are, and the target peaks designated before the addition of the additive can be certainly detected with the improved sensitivity. Furthermore, as compared to the additive post-placement method, the additive pre-mix method expedites an analysis of a sample since the number of process steps for dropping solutions onto a sample plate is the same as in the no-additive method.

THIRD EXAMPLE

<1. Test Microorganism>

*Salmonella enterica* (serotype: *Typhimurium*, NBRC 13245) cultured on LB agar at 37 degrees Celsius for 20 hours was used as the test microorganism.

<2-1. Preparation of Matrix Solutions>

The matrix-and-additive mixture solutions SA-1 and SA-2 were prepared using the same combinations of the solvent and matrix substances as in the second example.

<2-2. Preparation of Matrix-and-Additive Mixture Solutions>

The three kinds of matrix-and-additive mixture solutions SA-3, SA-4 and SA-5 were prepared using the same combinations of the solvent and matrix substances as in the first and second examples.

<2-3. Preparation of Additive Solution>

The additive solution A-1 was prepared using the same combination of the solvent and matrix additive as in the second example.

<3. Mass Spectrometric Analysis>

For the analysis of the samples, as in the first example, the MALDI time-of-flight mass spectrometer (MALDI-TOFMS, manufactured by Shimadzu Corporation under the trade name of AXIMA-Performance) operated in the linear mode (positive ion mode) was used, and the same method was used to acquire data.

<4. Preparation of Samples>

<4-1. Preparation of Sample by Additive Pre-mix Method>

(1) Initially, an amount of test microorganism corresponding to a few colonies was put in 10 µL of each of the three kinds of matrix-and-additive mixture solutions SA-3 to SA-5 to obtain microorganism suspensions of SA-3 to SA-5.

(2) Next, 0.5 µL of the matrix solution SA-1 was dropped in each well on a sample plate and dried. Then, one of the three microorganism suspensions of SA-3 to SA-5 (1.2 µL) was dropped onto the dried substance.

(3) Subsequently, the microorganism suspensions of SA-3 to SA-5 in the wells on the sample plate was dried, and the obtained crystal of the matrix-microorganism mixture was used as a sample.

<4-2. Preparation of Samples by Additive Post-Placement Method>

(1) Initially, an amount of test microorganism corresponding to a few colonies was put in 10 µL of the matrix solution SA-2 to obtain a microorganism suspension of SA-2.

(2) Next, 0.5 µL of the matrix solution SA-1 was dropped onto each well on a sample plate and dried. Then, 1.2 µL of the microorganism suspension of SA-2 was additionally dropped onto the dried substance.

(3) Subsequently, the microorganism suspension of SA-2 in the wells on the sample plate was dried. Then, 1 µL of the additive solution A-1 was dropped onto the dried substance and dried.

(4) The crystal of the matrix-microorganism mixture obtained in (3) was used as a sample.

<4-3. Preparation of Samples by No-Additive Method>

(1) Initially, an amount of test microorganism corresponding to a few colonies was put in 10 µL of the matrix solution SA-2 to obtain a microorganism suspension of SA-2.

(2) Next, 0.5 µL of the matrix solution SA-1 was dropped into each well on a sample plate and dried. Then, 1.2 µL of the microorganism suspension of SA-2 was additionally dropped onto the dried substance.

(3) Subsequently, the microorganism suspension of SA-2 in the wells was dried, and the obtained crystal of the matrix-microorganism mixture was used as a sample.

<5. Results>

FIGS. 10 to 14 show mass spectra obtained in the third example.

Figure 10:
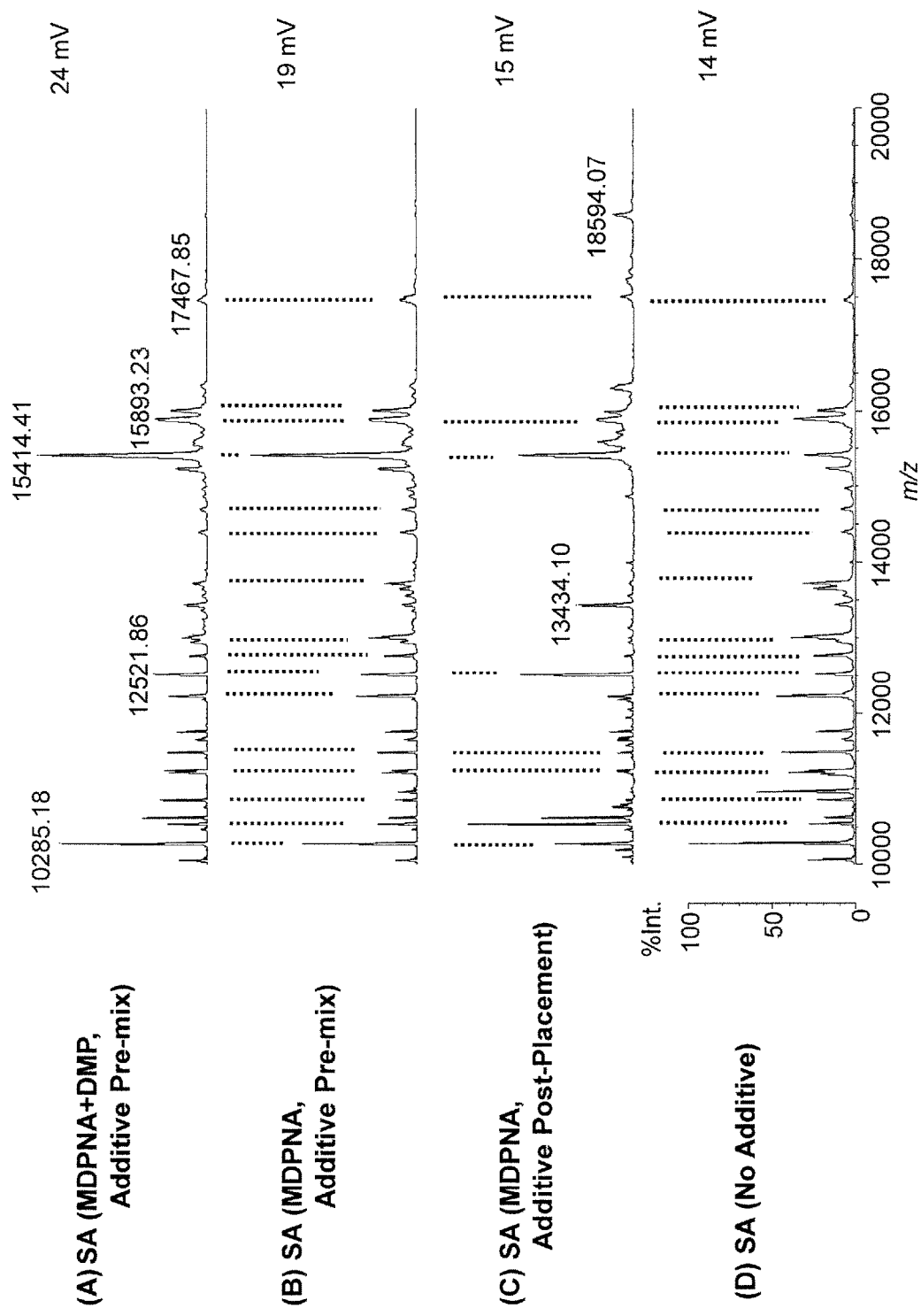
FIG. 10 is a chart showing a mass-to-charge-ratio range of m/z 10000 to 20000 in mass spectra obtained in the third example in which *Salmonella enterica* (serotype: *Typhimurium*, NBRC 13245) was used as the test microorganism.
Figure 11:
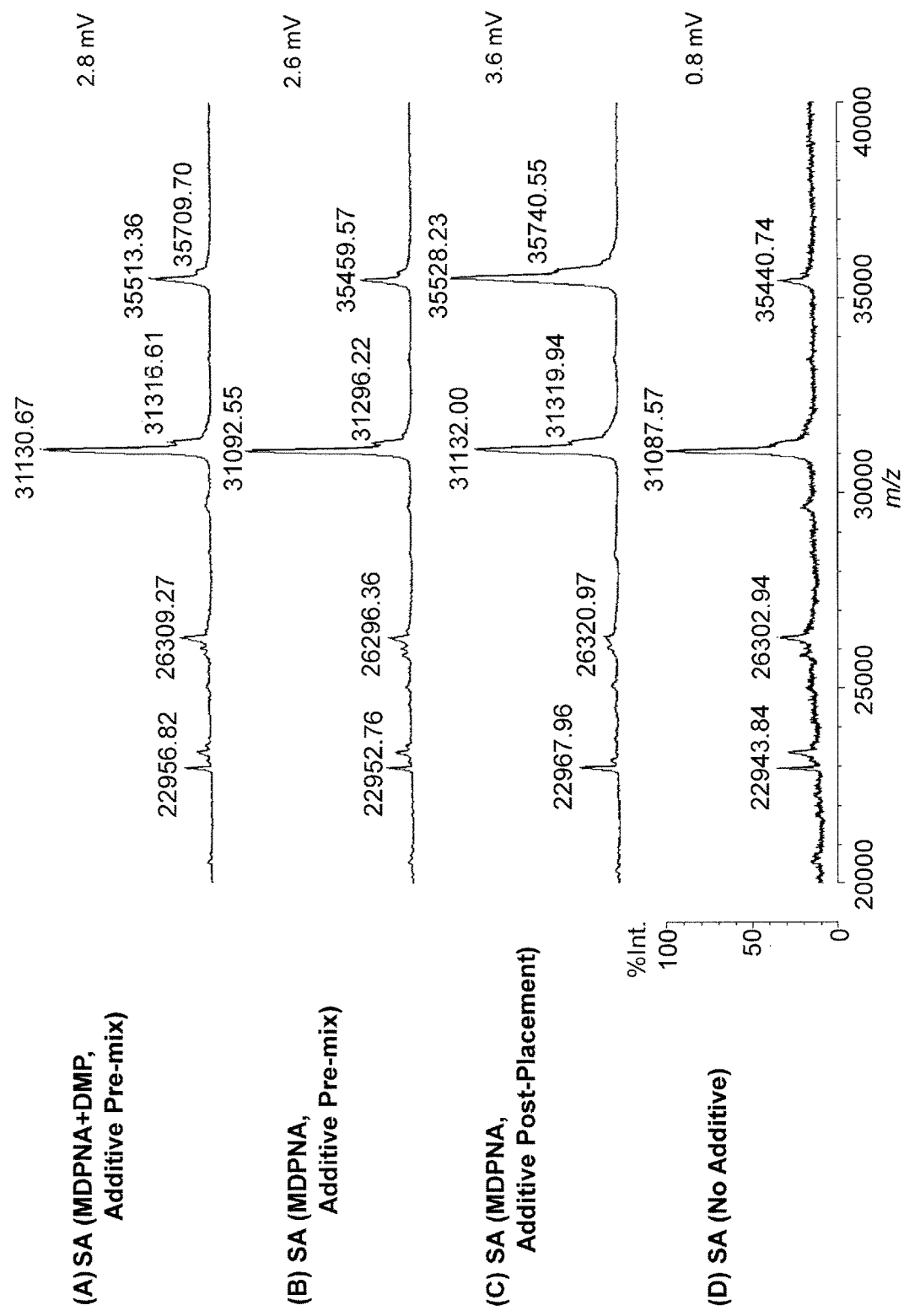
FIG. 11 is a chart showing a mass-to-charge-ratio range of m/z 20000 to 40000 in the mass spectra obtained in the third example in which *Salmonella enterica* (serotype: *Typhimurium*, NBRC 13245) was used as the test microorganism.
Figure 12:
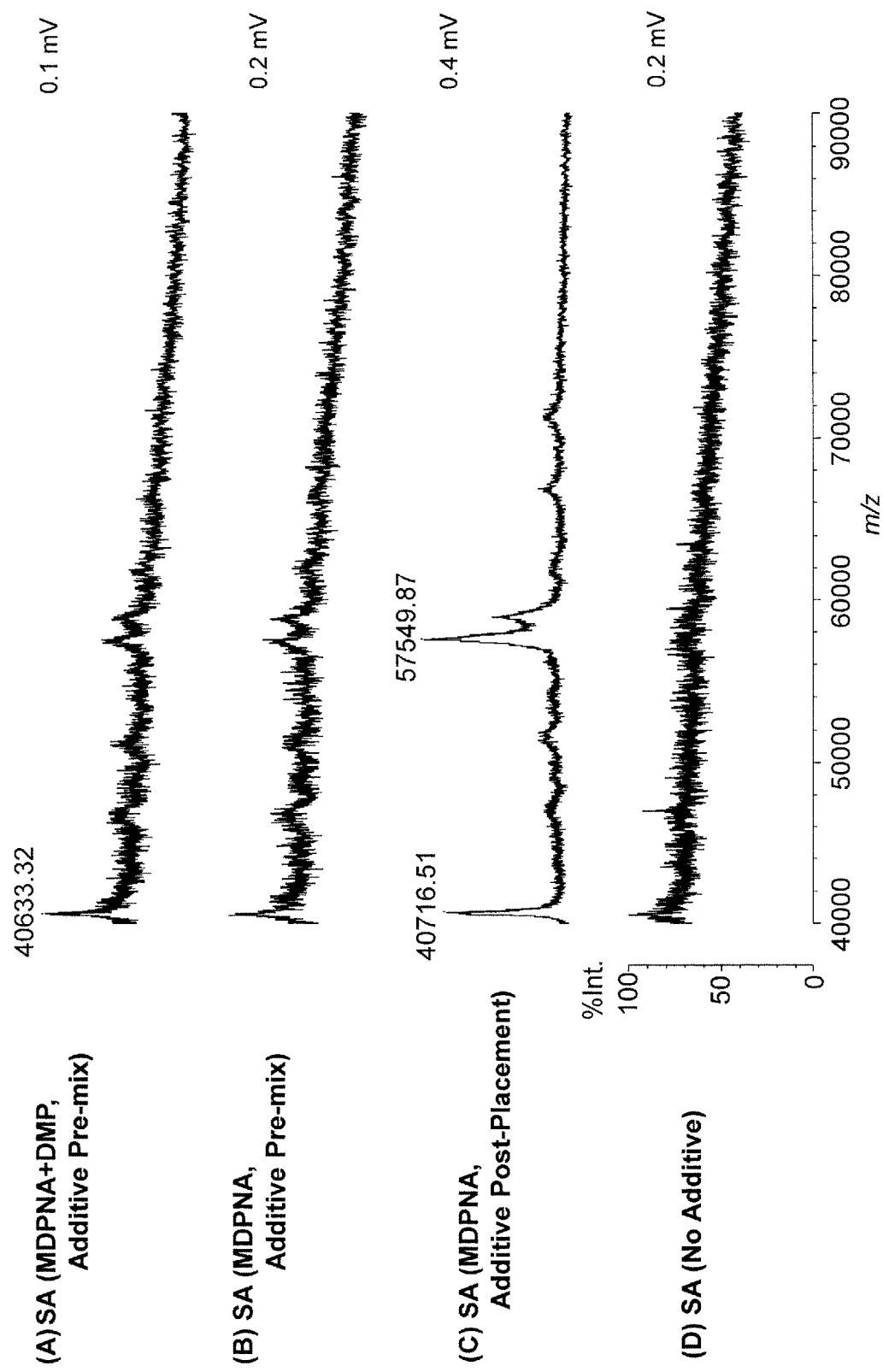
FIG. 12 is a chart showing a mass-to-charge-ratio range of m/z 40000 to 90000 in the mass spectra obtained in the third example in which *Salmonella enterica* (serotype: *Typhimurium*, NBRC 13245) was used as the test microorganism.

Charts (A) and (B) in each of FIGS. 10 to 12 are mass spectra obtained for samples prepared by the additive pre-mix methods in which SA-5 and SA-3 were respectively used as the matrix-and-additive mixture solution. Chart (C) in each of FIGS. 10 to 12 is a mass spectrum obtained for a sample prepared by the additive post-placement method using the additive solution A-1. Chart (D) in each of FIGS. 10 to 12 is a mass spectrum obtained for a sample prepared by the no-additive method.

FIG. 10 shows the mass spectra within a mass-to-charge-ratio range of m/z 10000 to 20000. FIG. 11 shows the mass spectra within a mass-to-charge-ratio range of m/z 20000 to 40000. FIG. 12 shows the mass spectra within a mass-to-charge-ratio range of m/z 40000 to 90000.

As shown in FIG. 10, within the mass-to-charge-ratio range of m/z 10000 to 20000, the mass spectrum (C) obtained by the additive post-placement method exhibited a slightly different peak profile from the mass spectrum (D) obtained by the no-additive method. By comparison, the mass spectra (A) and (B) obtained by the additive pre-mix methods both exhibited almost the same peak profile as the mass spectrum (D) obtained by the no-additive method.

Within the mass-to-charge-ratio range of m/z 20000 to 40000 shown FIG. 11 as well as the mass-to-charge-ratio range of m/z 40000 to 90000 in shown FIG. 12, an improvement in the peak intensity and signal-to-noise ratio was confirmed in the mass spectra (A), (B) and (C) obtained by the additive pre-mix methods and the additive post-placement method as compared to the mass spectrum (D) obtained by the no-additive method.

In particular, within a mass-to-charge-ratio range of m/z 40000 or higher, high-intensity peaks were observed in the mass spectrum obtained by the additive post-placement method (C).

Figure 13:
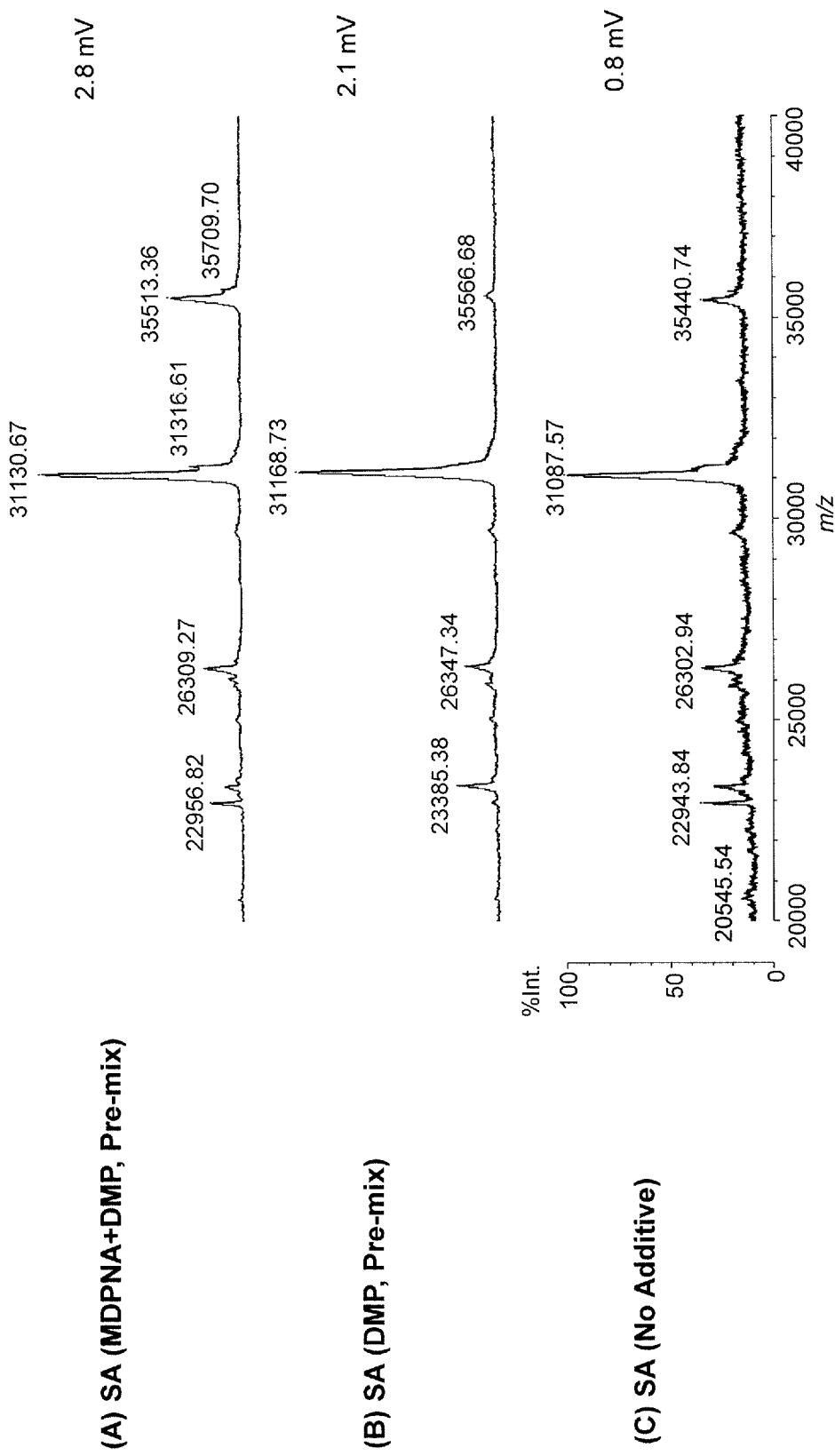
FIG. 13 is a chart showing a mass-to-charge-ratio range of m/z 20000 to 40000 in the mass spectra obtained in the third example in which *Salmonella enterica* (serotype: *Typhimurium*, NBRC 13245) was used as the test microorganism.
Figure 14:
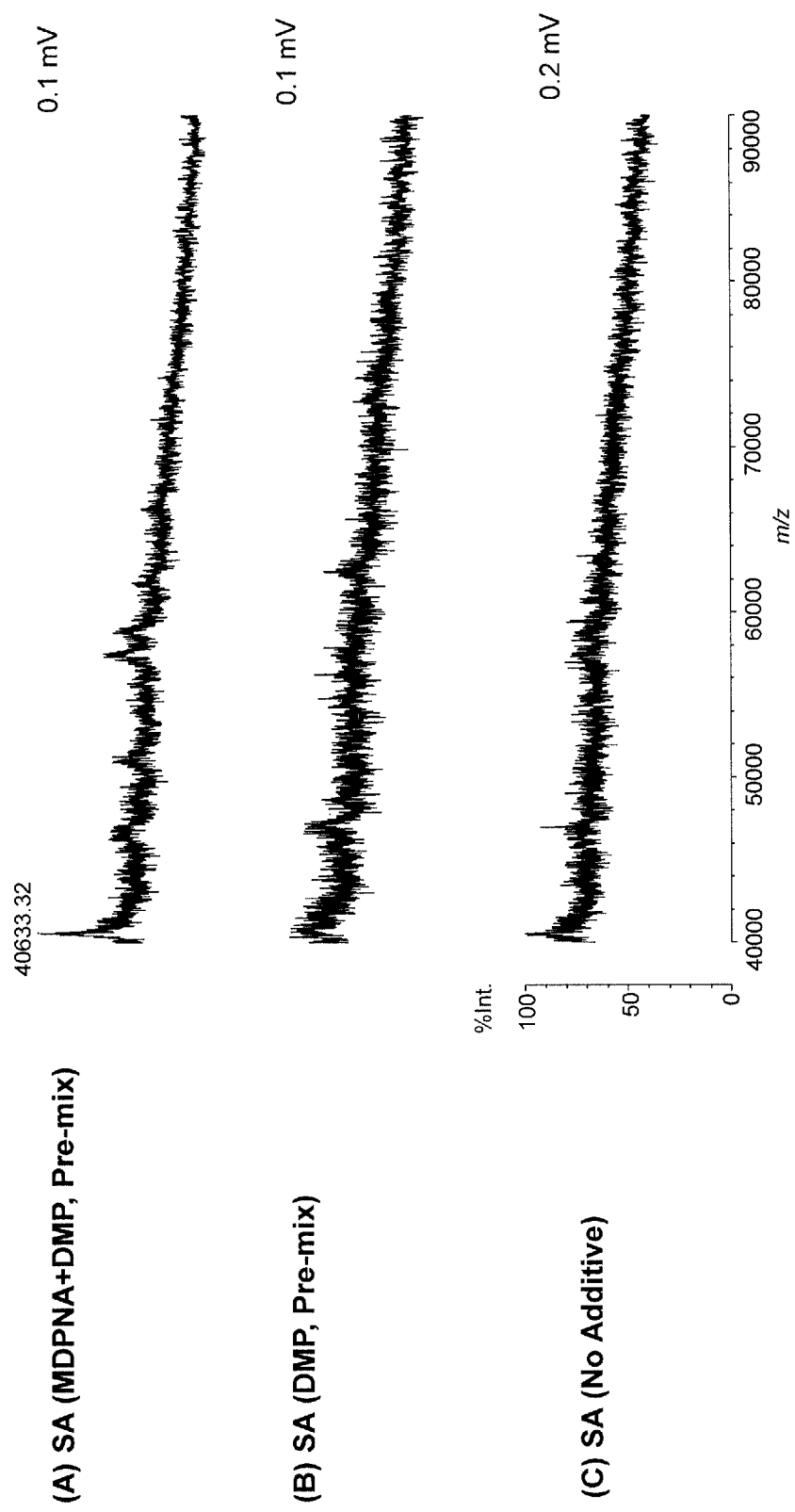
FIG. 14 is a chart showing a mass-to-charge-ratio range of m/z 40000 to 90000 in the mass spectra obtained in the third example in which *Salmonella enterica* (serotype: *Typhimurium*, NBRC 13245) was used as the test microorganism.

Charts (A) and (B) in each of FIGS. 13 and 14 are mass spectra obtained for samples prepared by the additive pre-mix methods in which SA-5 and SA-4 were respectively used as the matrix-and-additive mixture solution. Chart (C) in each of FIGS. 13 and 14 is a mass spectrum obtained for a sample prepared by the no-additive method. FIG. 13 shows the mass spectra within a mass-to-charge-ratio range of m/z 20000 to 40000. FIG. 14 shows the mass spectra within a mass-to-charge-ratio range of m/z 40000 to 90000.

As shown in FIG. 13, within the mass-to-charge-ratio range of m/z 20000 to 40000, the mass spectra (A) and (B) obtained by the additive pre-mix methods both exhibited the same peak profile as the mass spectrum (C) obtained by the no-additive method. Furthermore, an improvement in the peak intensity and signal-to-noise ratio was confirmed in the mass spectra (A) and (B) obtained by the additive pre-mix methods as compared to the mass spectrum (C) obtained by the no-additive method.

Additionally, within the mass-to-charge-ratio range of m/z 40000 to 90000 shown in FIG. 14, a slight yet certain improvement in the signal-to-noise ratio was confirmed in the mass spectrum (A) obtained by the additive pre-mix method as compared to the mass spectrum (C) obtained by the no-additive method.

The results described thus far demonstrate that the sample preparation by the additive pre-mix method is particularly effective for improving the sensitivity within a high-mass range. Since the improvement of the sensitivity is achieved with no change in the peak profile, there is no loss of peaks due to the suppression effect caused by a change in the order of peak intensity or other factors. This consequently produces favorable effects. For example, the self-calibration peaks which have been used before the addition of the additive can be continuously used as they are, and the target peaks designated before the addition of the additive can be certainly detected with the improved sensitivity. Furthermore, as compared to the additive post-placement method, the additive pre-mix method expedites an analysis of a sample since the number of process steps for dropping solutions onto a sample plate is the same as in the no-additive method.

FOURTH EXAMPLE

<1. Test Microorganism>

*Salmonella enterica* (serotype: Orion, jfrlSe 1402-15) cultured on LB agar at 37 degrees Celsius for 20 hours was used as the test microorganism.

<2-1. Preparation of Matrix Solutions>

The matrix-and-additive mixture solutions SA-1 and SA-2 were prepared using the same combinations of the solvent and matrix substances as in the second and third examples.

<2-2. Preparation of Matrix-and-Additive Mixture Solutions>

The three kinds of matrix-and-additive mixture solutions SA-3, SA-4 and SA-5 were prepared using the same combinations of the solvent and matrix substances as in the first and second examples.

<2-3. Preparation of Additive Solution>

The additive solution A-1 was prepared using the same combination of the solvent and matrix additive as in the second example.

<3. Mass Spectrometric Analysis>

For the analysis of the samples, as in the first example, the MALDI time-of-flight mass spectrometer (MALDI-TOFMS, manufactured by Shimadzu Corporation under the trade name of AXIMA-Performance) operated in the linear mode (positive ion mode) was used, and the same method was used to acquire data.

<4. Preparation of Samples>

<4-1. Preparation of Sample by Additive Pre-mix Method>

(1) Initially, an amount of test microorganism corresponding to a few colonies was put in 10 µL of each of the three kinds of matrix-and-additive mixture solutions SA-3 to SA-5 to obtain microorganism suspensions of SA-3 to SA-5.

(2) Next, 0.5 µL of the matrix solution SA-1 was dropped in each well on a sample plate and dried. Then, one of the three microorganism suspensions of SA-3 to SA-5 (1.2 µL) was dropped onto the dried substance.

(3) Subsequently, the microorganism suspensions of SA-3 to SA-5 in the wells on the sample plate was dried, and the obtained crystal of the matrix-microorganism mixture was used as a sample.

<4-2. Preparation of Samples by Additive Post-Placement Method>

(1) Initially, an amount of test microorganism corresponding to a few colonies was put in 10 µL of the matrix solution SA-2 to obtain a microorganism suspension of SA-2.

(2) Next, 0.5 µL of the matrix solution SA-1 was dropped onto each well on a sample plate and dried. Then, 1.2 µL of the microorganism suspension of SA-2 was additionally dropped onto the dried substance.

(3) Subsequently, the microorganism suspension of SA-2 in the wells on the sample plate was dried. Then, 1 µL of the additive solution A-1 or A-2 was dropped onto the dried substance and dried.

(4) The crystal of the matrix-microorganism mixture obtained in (3) was used as a sample.

<4-3. Preparation of Samples by No-Additive Method>

(1) Initially, an amount of test microorganism corresponding to a few colonies was put in 10 µL of the matrix solution SA-2 to obtain a microorganism suspension of SA-2.

(2) Next, 0.5 µL of the matrix solution SA-1 was dropped into each well on a sample plate and dried. Then, 1.2 µL of the microorganism suspension of SA-2 was additionally dropped onto the dried substance.

(3) Subsequently, the microorganism suspension of SA-2 in the wells was dried, and the obtained crystal of the matrix-microorganism mixture was used as a sample.

<5. Results>

Figure 15:
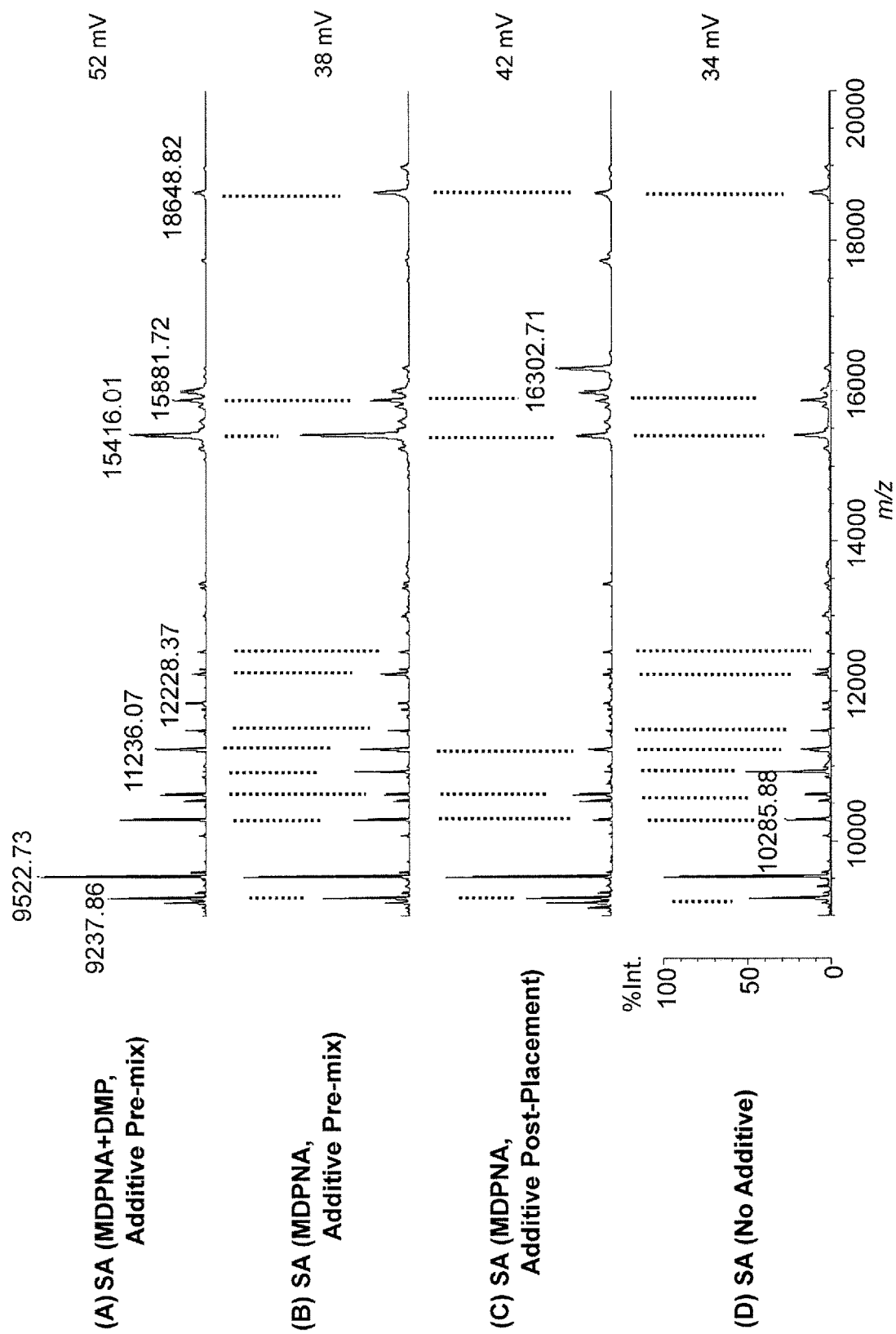
FIG. 15 is a chart showing a mass-to-charge-ratio range of m/z 9000 to 20000 in mass spectra obtained in the fourth example in which *Salmonella enterica* (serotype: Orion, jfrlSe 1402-15) was used as the test microorganism.
Figure 16:
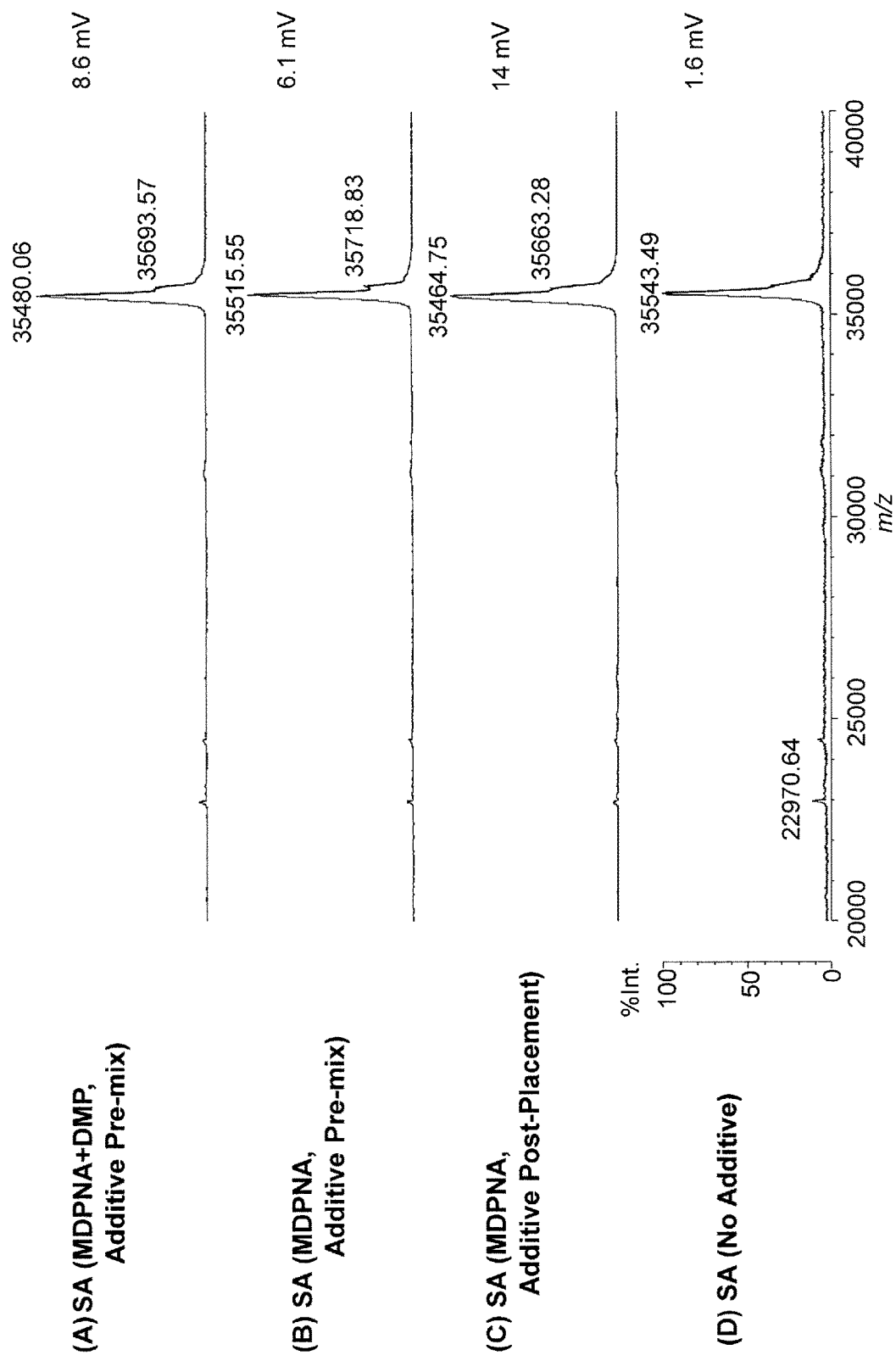
FIG. 16 is a chart showing a mass-to-charge-ratio range of m/z 20000 to 40000 in the mass spectra obtained in the fourth example in which *Salmonella enterica* (serotype: Orion, jfrlSe 1402-15) was used as the test microorganism.
Figure 17:
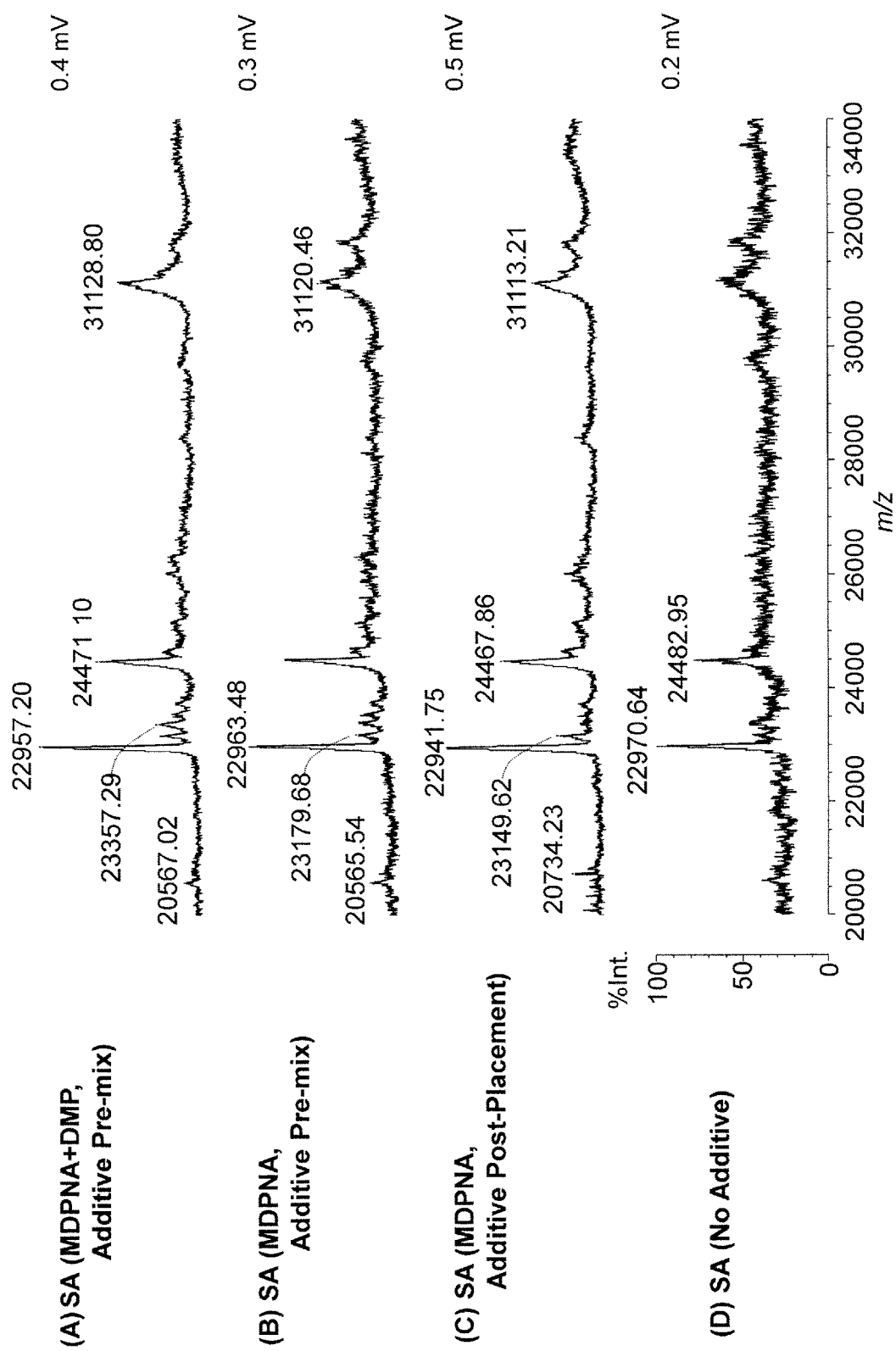
FIG. 17 is a chart showing a mass-to-charge-ratio range of m/z 20000 to 34000 in the mass spectra obtained in the fourth example in which *Salmonella enterica* (serotype: Orion, jfrlSe 1402-15) was used as the test microorganism.
Figure 18:
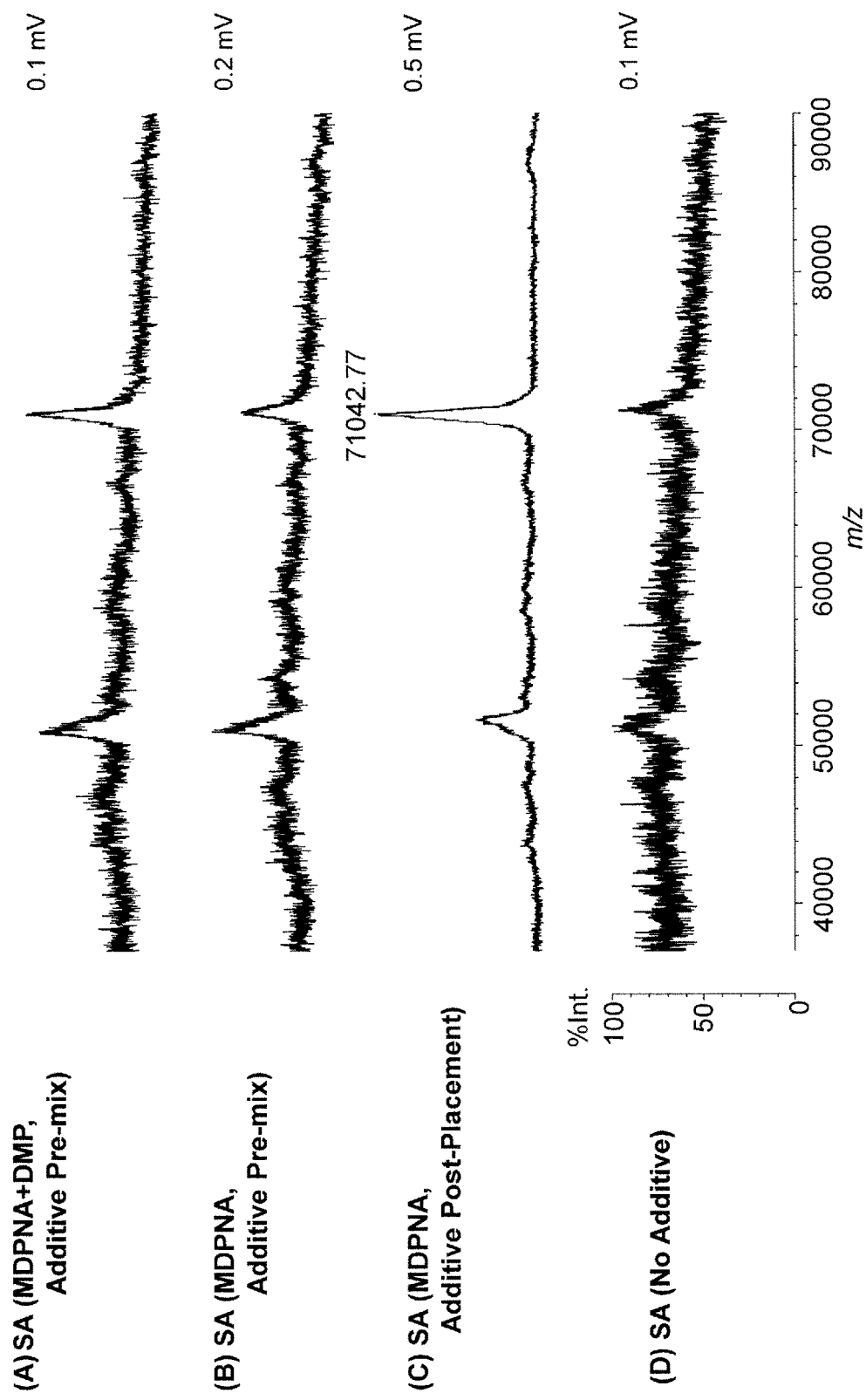
FIG. 18 is a chart showing a mass-to-charge-ratio range of m/z 38000 to 90000 in the mass spectra obtained in the fourth example in which *Salmonella enterica* (serotype: Orion, jfrlSe 1402-15) was used as the test microorganism.

FIGS. 15 to 21 show mass spectra obtained in the fourth example. Charts (A) and (B) in each of FIGS. 15 to 18 are mass spectra obtained for samples prepared by the additive pre-mix methods in which SA-5 and SA-3 were respectively used as the matrix-and-additive mixture solution. Chart (C) in each of FIGS. 15 to 18 is a mass spectrum obtained for a sample prepared by the additive post-placement method in which the additive solution A-1 was used. Chart (D) in each of FIGS. 15 to 18 is a mass spectrum obtained for a sample prepared by the no-additive method. FIG. 15 shows the mass spectra within a mass-to-charge-ratio range of m/z 9000 to 20000. FIG. 16 shows the mass spectra within a mass-to-charge-ratio range of m/z 20000 to 40000. FIG. 17 shows the mass spectra within a mass-to-charge-ratio range of m/z 20000 to 34000. FIG. 18 shows the mass spectra within a mass-to-charge-ratio range of m/z 37000 to 90000.

As shown in FIG. 15, within the mass-to-charge-ratio range of m/z 9000 to 20000, the mass spectrum (C) obtained by the additive post-placement method exhibited a slightly different peak profile from the mass spectrum (D) obtained by the no-additive method. By comparison, the mass spectra (A) and (B) obtained by the additive pre-mix methods both exhibited almost the same peak profile as the mass spectrum (D) obtained by the no-additive method.

Within the mass-to-charge-ratio range of m/z 20000 to 40000 shown in FIG. 16 as well as the mass-to-charge-ratio range of m/z 20000 to 34000 shown in FIG. 17, an improvement in the peak intensity or signal-to-noise ratio was confirmed in the mass spectra (A), (B) and (C) obtained by the additive pre-mix methods and the additive post-placement method as compared to the mass spectrum (D) obtained by the no-additive method.

Within the mass-to-charge-ratio range of m/z 37000 to 90000 shown in FIG. 18, an improvement in the peak intensity or signal-to-noise ratio was confirmed in the mass spectra (A), (B) and (C) obtained by the additive pre-mix methods and the additive post-placement method as compared to the mass spectrum (D) obtained by the no-additive method. In particular, within a mass-to-charge-ratio range of m/z 40000 or higher, the peaks were detected with high sensitivity by the additive post-placement method (C).

Figure 19:
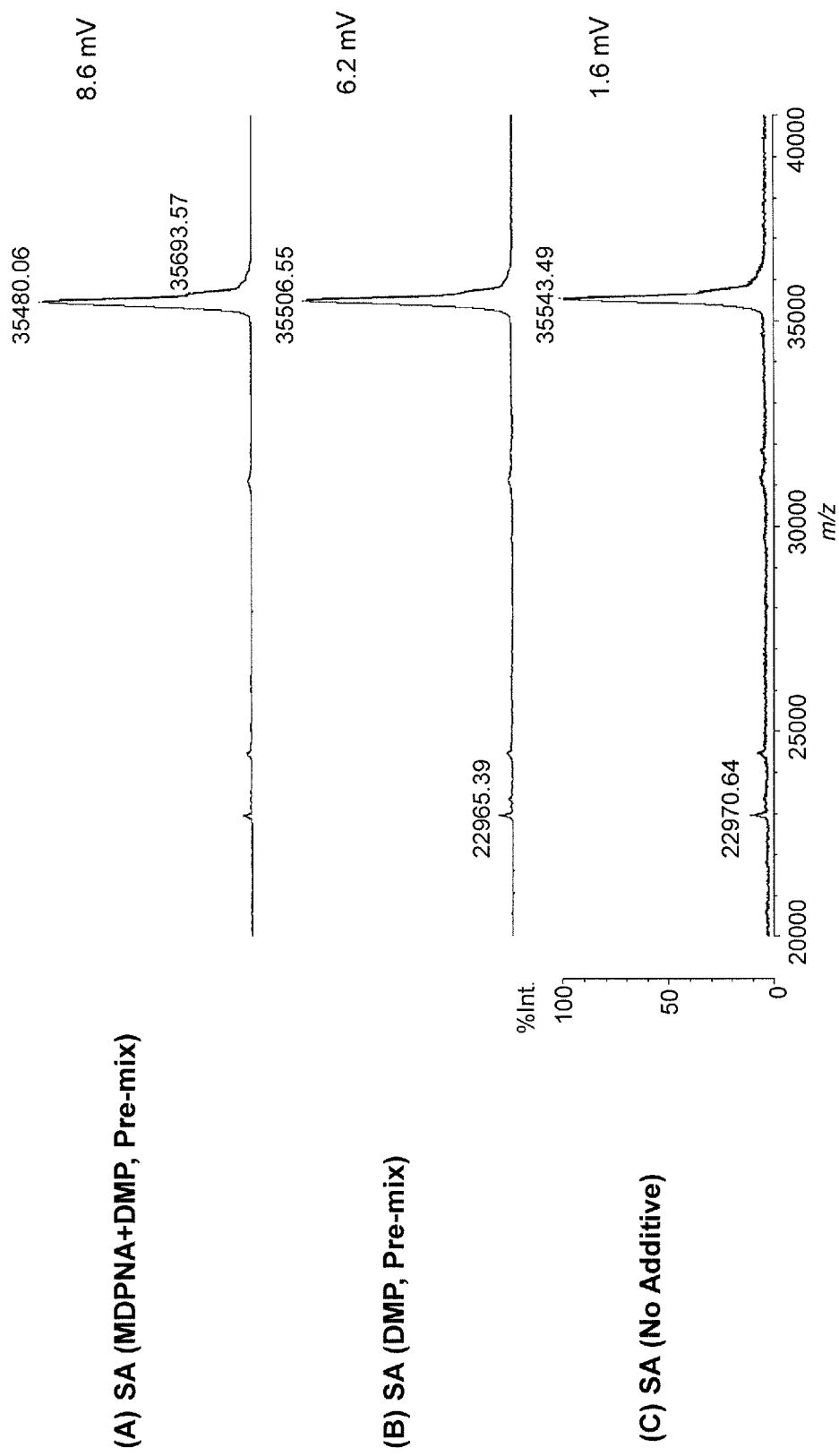
FIG. 19 is a chart showing a mass-to-charge-ratio range of m/z 20000 to 40000 in the mass spectra obtained in the fourth example in which *Salmonella enterica* (serotype: Orion, jfrlSe 1402-15) was used as the test microorganism.
Figure 20:
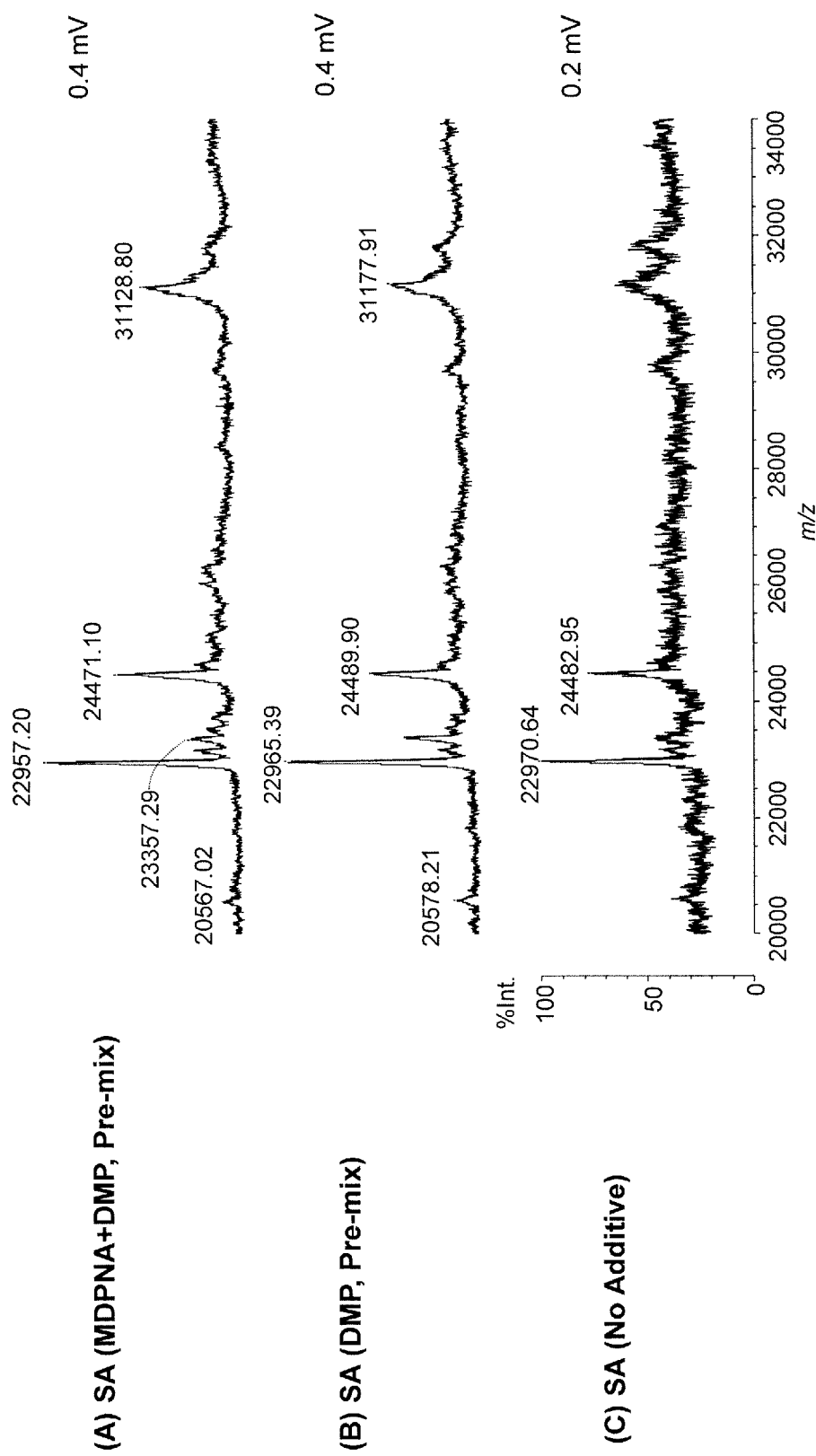
FIG. 20 is a chart showing a mass-to-charge-ratio range of m/z 20000 to 34000 in the mass spectra obtained in the fourth example in which *Salmonella enterica* (serotype: Orion, jfrlSe 1402-15) was used as the test microorganism.
Figure 21:
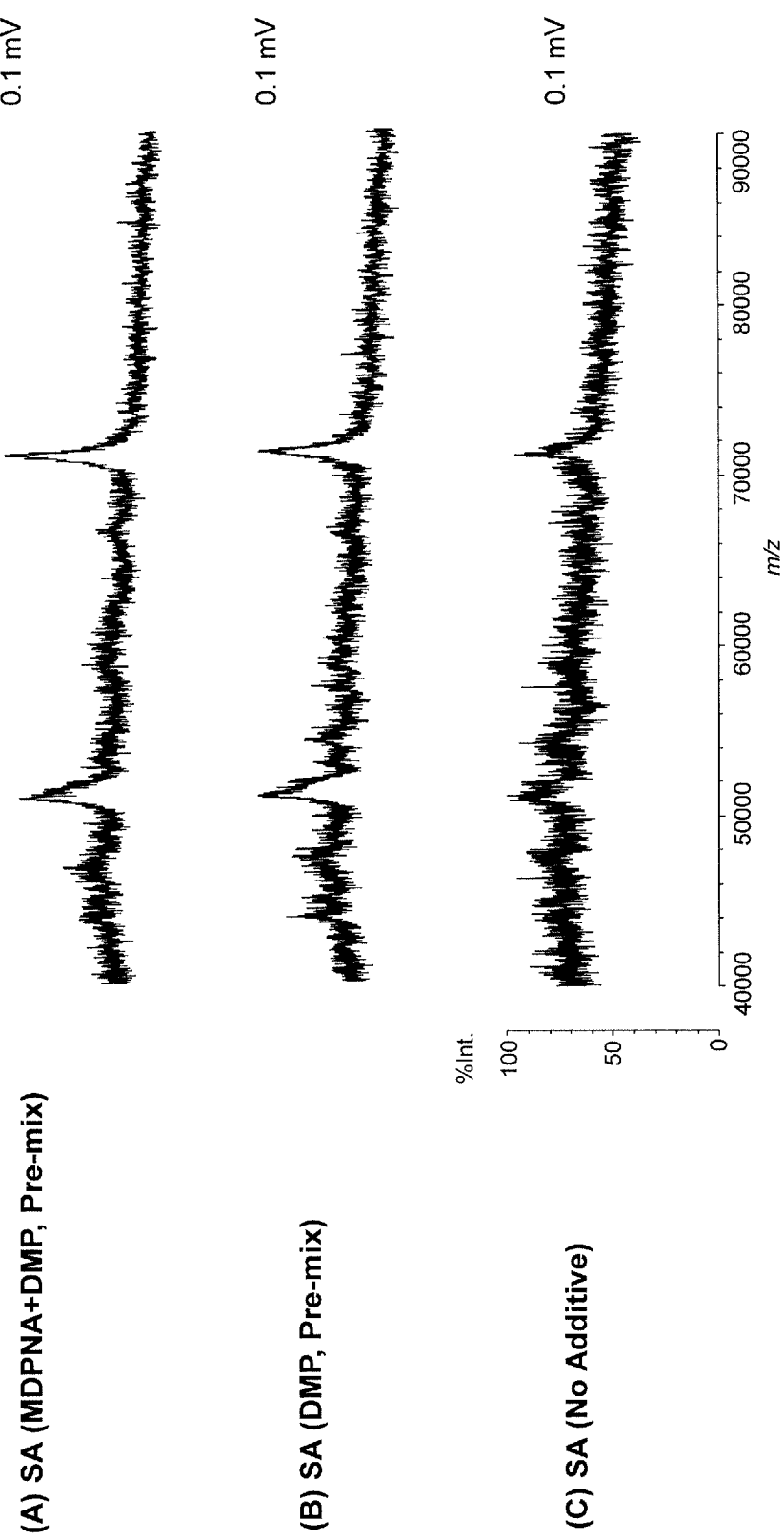
FIG. 21 is a chart showing a mass-to-charge-ratio range of m/z 40000 to 90000 in the mass spectra obtained in the fourth example in which *Salmonella enterica* (serotype: Orion, jfrlSe 1402-15) was used as the test microorganism.

Charts (A) and (B) in each of FIGS. 19 to 21 are mass spectra obtained for samples prepared by the additive pre-mix methods in which SA-5 and SA-4 were respectively used as the matrix-and-additive mixture solution. Chart (C) in each of FIGS. 19 to 21 is a mass spectrum obtained for a sample prepared by the no-additive method. FIG. 19 shows the mass spectra within a mass-to-charge-ratio range of m/z 20000 to 40000. FIG. 20 shows the mass spectra within a mass-to-charge-ratio range of m/z 20000 to 34000. FIG. 21 shows the mass spectra within a mass-to-charge-ratio range of m/z 40000 to 90000.

Within the mass-to-charge-ratio range of m/z 20000 to 40000 shown in FIG. 19 as well as the mass-to-charge-ratio range of m/z 20000 to 34000 shown in FIG. 20, the mass spectra (A) and (B) obtained by the additive pre-mix methods both exhibited the same peak profile as the mass spectrum (C) obtained by the no-additive method. Furthermore, an improvement in the peak intensity or signal-to-noise ratio was confirmed in the mass spectra (A) and (B) obtained by the additive pre-mix methods as compared to the mass spectrum (C) obtained by the no-additive method.

Furthermore, within the mass-to-charge-ratio range of m/z 40000 to 90000 shown in FIG. 21, an improvement in the peak intensity or signal-to-noise ratio was confirmed in the mass spectra (A) and (B) obtained by the additive pre-mix methods as compared to the mass spectrum (C) obtained by the no-additive method.

The results described thus far demonstrate that the sample preparation by the additive pre-mix method is particularly effective for improving the sensitivity within a high-mass range. Since the improvement of the sensitivity is achieved with no change in the peak profile, there is no loss of peaks due to the suppression effect caused by a change in the order of peak intensity or other factors. This consequently produces favorable effects. For example, the self-calibration peaks which have been used before the addition of the additive can be continuously used as they are, and the target peaks designated before the addition of the additive can be certainly detected with the improved sensitivity. Furthermore, as compared to the additive post-placement method, the additive pre-mix method expedites an analysis of a sample since the number of process steps for dropping solutions onto a sample plate is the same as in the no-additive method.

The invention claimed is:

1. A method for analyzing a microorganism using a matrix assisted laser desorption/ionization mass spectrometer, wherein the method comprises forming a mixture of a matrix-and-additive mixture solution and a test microorganism, wherein the matrix-and-additive mixture solution comprises a) an alkylphosphonic acid and/or a surfactant, and b) a matrix substance, wherein the mixture is formed by preparing a matrix-microorganism mixture comprising the matrix-and-additive mixture solution and the test microorganism, and then dropping the matrix-microorganism mixture on a sample plate, and analyzing the mixture comprising the test microorganism in a matrix assisted laser desorption/ionization spectrometer.

2. The method for analyzing a microorganism according to claim 1, wherein the alkylphosphonic acid is methylenediphosphonic acid.

3. The method for analyzing a microorganism according to claim 2, wherein the surfactant is decyl-β-D-maltopyranoside.

4. The method for analyzing a microorganism according to claim 3, wherein the matrix substance is sinapinic acid.

5. The method for analyzing a microorganism according to claim 2, wherein the matrix substance is sinapinic acid.

6. The method for analyzing a microorganism according to claim 1, wherein the surfactant is decyl-β-D-maltopyranoside.

7. The method for analyzing a microorganism according to claim 6, wherein the matrix substance is sinapinic acid.

8. The method for analyzing a microorganism according to claim 1, wherein the matrix substance is sinapinic acid.

9. The method for analyzing a microorganism according to claim 8, wherein sinapinic acid is present in an amount of 10 to 30 mg/mL, the alkylphosphonic acid is 0.1 to 5% of methylenediphosphonic acid and the surfactant is 0.1 to 10 mM of decyl-β-D-maltopyranoside in an aqueous solution containing 30 to 70% of acetonitrile and 0.1 to 3% of trifluoroacetic acid.

10. The method for analyzing a microorganism according to claim 1, wherein the matrix substance is present in an amount of 10 to 30 mg/mL, the alkylphosphonic acid is 0.1 to 5% of methylenediphosphonic acid and the surfactant is 0.1 to 10 mM of decyl-β-D-maltopyranoside in an aqueous solution containing 30 to 70% of acetonitrile and 0.1 to 3% of trifluoroacetic acid.

11. The method for analyzing a test microorganism according to claim 1, further comprising steps of: obtaining a mass spectrum for a sample containing the test microorganism, the mass spectrum covering a mass range including a high-mass range of m/z 10000 or higher in mass-to-charge ratio; comparing the mass spectrum with mass-spectrum patterns stored in a database; and identifying the test microorganism based on a result obtained by comparing the mass spectrum with the mass-spectrum patterns.

\* \* \* \* \*